(12) United States Patent
Akselrod et al.

(10) Patent No.: US 6,280,390 B1
(45) Date of Patent: Aug. 28, 2001

(54) SYSTEM AND METHOD FOR NON-INVASIVELY MONITORING HEMODYNAMIC PARAMETERS

(75) Inventors: Solange Akselrod, Givat Shmuel; Amir Schechter, Kfar Saba, both of (IL)

(73) Assignee: Ramot University Authority for Applied Research and Industrial Development Ltd., Tel-Aviv (IL)

( * ) Notice: Subject to any disclaimer, the term of this patent is extended or adjusted under 35 U.S.C. 154(b) by 0 days.

(21) Appl. No.: 09/473,652

(22) Filed: Dec. 29, 1999

(51) Int. Cl.$^7$ ........................................................ A61B 5/00
(52) U.S. Cl. ............................ 600/485; 600/500; 600/475
(58) Field of Search ................................... 600/485, 500, 600/513, 504, 479

(56) References Cited

U.S. PATENT DOCUMENTS

| | | |
|---|---|---|
| 4,269,193 | 5/1981 | Eckerle . |
| 4,406,289 | 9/1983 | Wesseling et al. . |
| 4,423,738 | 1/1984 | Newgard . |
| 4,475,554 | 10/1984 | Hyndman . |
| 4,510,940 | 4/1985 | Wesseling . |
| 4,524,777 | 6/1985 | Kisioka et al. . |
| 4,539,997 | 9/1985 | Wesseling et al. . |
| 4,669,485 | 6/1987 | Russell . |
| 4,718,426 | 1/1988 | Russell . |
| 4,718,427 | 1/1988 | Russell . |
| 4,718,428 | 1/1988 | Russell . |
| 4,779,491 | 10/1988 | Fujiwara . |
| 4,802,488 | 2/1989 | Eckerle . |
| 4,846,189 | 7/1989 | Sun . |
| 4,869,261 | 9/1989 | Penaz . |
| 4,960,128 | 10/1990 | Gordon et al. . |
| 5,165,416 | 11/1992 | Shinoda et al. . |
| 5,237,997 | * 8/1993 | Gruebel et al. ...................... 600/500 |
| 5,396,895 | * 3/1995 | Takashima et al. .................. 600/500 |
| 5,617,869 | * 4/1997 | Austin et al. ........................ 600/500 |
| 5,649,543 | * 7/1997 | Hosaka et al. ....................... 600/500 |
| 5,755,669 | * 5/1998 | Ono et al. ............................. 600/500 |
| 5,862,805 | 1/1999 | Nitzan . |

FOREIGN PATENT DOCUMENTS

| | | |
|---|---|---|
| 048 060 B1 | 8/1981 | (EP) . |
| 443 267 A1 | 12/1990 | (EP) . |

\* cited by examiner

*Primary Examiner*—Robert L. Nasser

(57) ABSTRACT

A system for non-invasively monitoring at least one hemodynamic vascular parameter of an individual is disclosed. The system comprises (a) at least two infrared detectors being positionable in a spaced apart configuration against a region of a skin of the individual above at least one blood vessel, each of said at least two infrared detectors being for individually collecting infrared spectral data from said region of the skin, said infrared spectral data corresponding to a volume of blood present within said at least one blood vessel; and (b) a processing unit being in communication with said at least two infrared detectors, said processing unit being for independently processing said infrared spectral data collected by each of said at least two infrared detectors so as to yield information pertaining to the at least one hemodynamic vascular parameter of the individual.

30 Claims, 14 Drawing Sheets

SYSTEM AND METHOD FOR NON-INVASIVELY MONITORING HEMODYNAMIC PARAMETERS

FIELD AND BACKGROUND OF THE INVENTION

The present invention relates to a system and method for monitoring hemodynamic vascular parameters of a patient and, more particularly, to a system and method utilizing photoplethysmography to monitor parameters associated with, for example, blood pressure and blood flow of a patient.

Hemodynamic vascular parameters such as blood pressure, blood flow and the like which are typically measured using non-invasive procedures are routinely monitored by physicians in order to determine the physiological state of the heart and circulatory system of a patient. Of these hemodynamic vascular parameters, blood pressure is the most commonly monitored.

Blood pressure is the force within the circulatory system of an individual that ensures a flow of blood and delivery of oxygen and nutrients to the tissue.

Abnormal blood pressure readings and/or blood pressure fluctuations over time are oftentimes indicative of heart or circulatory disorders. Hypertension is one of the most common diseases in the adult population, often accompanied by secondary cardiovascular damage. In addition, prolonged reduction or loss of pressure severely limits the amount of tissue perfusion and could therefore result in damage to, or even death of, the tissue. Although some tissues can tolerate hypoperfusion for fairly long periods of time, the brain, heart and kidneys are very sensitive to a reduction in blood flow. Thus, blood pressure is a frequently monitored both routinely and also during surgical procedures where ample supply of blood to tissues is crucial for tissue survival.

During and after surgery, blood pressure is affected by the type of surgery and physiological factors such as the body's response to the surgery. Moreover, during and after surgery, blood pressure is manipulated and controlled using various medications. Often, these physiological factors and the given medications result in a situation requiring immediate blood pressure measurement, and corrective action.

In some clinical situations, dramatic changes in blood pressure can occur instantaneously. For example, a sudden change in pressure may occur due to a reaction to drug therapy. Also, patient reactions to the surgery, sudden occlusion of an artery due to an embolism, or even sudden cardiac arrest are a few of the possibilities. It is very important to detect these sudden changes immediately, and to insure that the direction and amount of the changes be accurate within certain limits. Conversely, it is equally important that false indications of significant blood pressure changes do not occur.

Due to the above described reasons, constant monitoring of blood pressure of a patient is often necessary. The traditional method of measuring blood pressure is with the use of a occlusive cuff, a stethoscope and a pressure manometer. However, this technique is slow, subjective in nature, requires the intervention of a skilled clinician and does not provide the timely readings frequently required in critical situations.

For these reasons, two methods of measuring blood pressure have been developed: invasive, continuous (beat-to-beat) measurements and noninvasive, intermittent methods that use an automated occlusive cuff device.

Invasive methods suffer from several inherent limitations including the risk of embolization, nerve damage, infection, bleeding and vessel wall damage. In addition due to their invasive nature such methods are more suitable to blood pressure monitoring during surgical procedures.

The noninvasive cuff method does not have the inherent disadvantages of the invasive technique, however it also does not provide the continuous beat-to-beat pressure variations obtainable with the invasive method. Further, the noninvasive cuff method typically requires 15 to 45 seconds to obtain a measurement, and since it is an occlusive technique, the method should allow a minimum of 15 seconds to ensure sufficient venous recovery. Thus, at best there is typically ½ to 1 minute between updated pressure measurements. When fast acting medications are administered, this is an inordinately long amount of time to wait for an updated pressure reading. Also, frequent cuff inflation over extended periods of time may result in ecchymosis and/or nerve damage in the area underlying the cuff.

Several systems have been developed to address the need for continuous, noninvasive blood pressure measurement.

European Patent Document 0048060 and U.S. Pat. Nos. 4,406,289, 4,510,940 and 4,539,997 to Wesseling et al., U.S. Pat. No. 4,475,554 to Hyndman, U.S. Pat. No. 4,524,777 (1985) to Kisioka, U.S. Pat. No. 4,846,189 to Sun and U.S. Pat. No. 4,869,261 to Penaz, all relate to methods and devices utilizing a technique known as photoplethysmography which is commercially implemented in a device known as the FINAPRES system (Omeda).

The FINAPRES system uses a small inflatable air cuff containing an infrared photoplethysmograph. The cuff is applied to one of the subject's fingers or thumb, and the photoplethysmograph measures the absorption at a wavelength specific for hemoglobin. The device first measures the individual's mean arterial pressure, and then varies the cuff pressure around the finger to maintain the transmural pressure at zero as determined by the photoplethysmograph. The device tracks the intra-arterial pressure wave by adjusting the cuff pressure to maintain the optical absorption constant at all times.

There are several major disadvantages to this technique. The signal amplitude detected by the photoplethysmograph is a function of the changes in the diameter of the artery within the finger, and is determined by the compliance characteristics of the artery. The device maintains this amplitude at a constant value. This value, or set point, must correspond to the point of zero transmural stress in order to determine the correct pressure. During surgery for example, the device cannot differentiate between changes in photoplethysmograph amplitude due to intra-arterial pressure changes and those due to arterial wall compliance changes. Consequently, the FINAPRES system cannot accurately respond to pressure changes caused by changes in vasomotor tone. In addition, maintaining continuous cuff pressure causes restriction of the circulation in the finger being used, which is uncomfortable when maintained for extended periods of time such as during surgery or during a stay in an intensive care unit.

U.S. Pat. Nos. 4,669,485, 4,718,426, 4,718,427 and 4,718,428 all to Russel, describe a device using a conventional blood pressure cuff applied to a person's upper arm to sense an oscillometric signal. The subject's blood pressure is obtained initially by the oscillometric technique, and then changes in the oscillometric signal indicate changes from this initial reference pressure.

There are two inherent limitations to this device. First, the use of a large air bag as the sensing device provides a means for detecting the fundamental and lower harmonics of the blood pressure signal (up to a few Hertz), but also acts to attenuate many higher order harmonics containing key information relating to blood pressure variations. Second, the use of a cuff to detect the oscillometric signal creates a signal that is very sensitive to patient movement. Since patient movement is often encountered during surgery or in critical care situations, the device requires frequent recalibration to be accurate.

U.S. Pat. Nos. 4,269,193, 4,799,491 and 4,802,488 to Eckerle, U.S. Pat. No. 4,423,738 to Newgard, and U.S. Pat. No. 5,165,416 to Shinoda et al., all describe methods and devices for detecting the pressure wave in the underlying artery of an individual using a technique known as the tonometric technique.

These device and methods utilize a multi-element piezoresistive detector to noninvasively detect the blood pressure wave at the radial artery. This signal is then processed and changes in its amplitude are used to interpret changes to the pressure values obtained using the conventional oscillometric technique.

A major drawback to this technique lies in the method of interpreting changes to the waveform signal. Reliance solely on amplitude changes is misleading since the signal amplitude may increase or decrease with an increase in blood pressure, etc. Secondly, it is dependent on the artery being exactly flat, and variations in artery flatness can introduce errors. It also assumes that the selected sensing element is small with respect to the artery, and that it does not move from its position centered over the artery. Thus, any movement such as that often encountered in surgery or critical care situations will reduce the accuracy of this device.

European Patent Document 0 443 267 A 1 to Smith, describes a technique for monitoring changes in pulse transit time to provide a continuous, noninvasive measure of blood pressure. This technique was developed by Sentinel Monitoring, Inc., of Indianapolis, Ind., and uses a duplicity of photometric detectors similar to those used with oximeters. Typically, one detector is applied to the subject's ear lobe, and the other to a finger. The detectors are used for determining changes in the arrival time of the pulse at each of these sites, and to determine changes in local blood volume. Following an initial calibration pressure measurement obtained with a conventional blood pressure cuff, the Smith device adjusts these pressures by interpreting changes in the pulse transit time and in the optical density of the photoplethysmograph signal.

There are two disadvantages to the Smith technique. First, changes in pulse transit time are very small along major arteries. As a result, small errors caused by patient movement or noise render questionable data. Second, small variations in photoplethysmographic waveform morphology or detector noise can generate measurement errors greater than the sensitivity of the technique to changes in blood pressure.

U.S. Pat. No. 4,960,128 to Gordon, et al., describes a method of determining blood pressure by measuring a single harmonic of the frequencies and displacements of the patient's arterial wall. In Gordon, initial (absolute) blood pressure values are obtained with a cuff and stethoscope or via an intermittent automated cuff machine, and manually entered into the device as initial reference values. A continuous detector signal is supplied by a noninvasive detector attached to the patient's skin above an artery. The detector signal is filtered, amplified and then sampled. This time sampled detector data is then Fourier transformed into the frequency domain and normalized.

As blood pressure changes, the reported frequencies and their relative amplitudes change. A comparison is made between the fundamental frequency of the present signal and the initial signal. For each shift in frequency (+or −) of 1 Hz, the offset is adjusted correspondingly to yield a change of 5 mm Hg. Thus, Gordon shows a device in which the patient's blood pressure is determined based on the difference in position of the fundamental frequency of the detector signal and initial signal.

The technique described by Gordon does not adequately account for the plurality of factors that can reflect a change in blood pressure. There is a multitude of waveshapes that can accompany a given set of blood pressure values, and the Gordon technique is limited by its function of comparing the frequency with the maximum amplitude of the current signal to that of the initial signal to determine blood pressure.

There is thus a widely recognized need for, and it would be highly advantageous to have, a system and method for accurately and noninvasively monitoring continuous beat-to-beat blood pressure and other important hemodynamic vascular parameters of a patient which is devoid of the above limitations.

SUMMARY OF THE INVENTION

According to one aspect of the present invention there is provided a system for non-invasively monitoring at least one hemodynamic vascular parameter of an individual, the system comprising (a) at least two infrared detectors being positionable in a spaced apart configuration against a region of a skin of the individual above at least one blood vessel, each of said at least two infrared detectors being for individually collecting infrared spectral data from said region of the skin, said infrared spectral data corresponding to a volume of blood present within said at least one blood vessel, and (b) a processing unit being in communication with said at least two infrared detectors, said processing unit being for independently processing said infrared spectral data collected by each of said at least two infrared detectors so as to yield information pertaining to the at least one hemodynamic vascular parameter of the individual.

According to another aspect of the present invention there is provided a method of non-invasively monitoring at least one hemodynamic vascular parameter of an individual, the method comprising the steps of (a) positioning at least two infrared detectors in a spaced apart configuration against a region of a skin of the individual above at least one blood vessel; (b) individually collecting in each of said infrared detectors, infrared spectral data from said region of the skin, said infrared spectral data corresponding to a volume of blood present within said at least one blood vessel; and (b) independently processing said infrared spectral data collected by each of said at least two infrared detectors so as to yield information pertaining to the at least one hemodynamic vascular parameter of the individual.

According to further features in preferred embodiments of the invention described below, each of said at least two infrared detectors detects changes in infrared reflection from said region of said skin.

According to still further features in the described preferred embodiments each of said at least two infrared detectors includes an infrared source for irradiating said region of said skin and an infrared sensor for sensing infrared reflection reflected from said region of the skin.

According to still further features in the described preferred embodiments said infrared source irradiates said region with infrared radiation of a wavelength within a range of 800 nm to 960 nm.

According to still further features in the described preferred embodiments each of said at least two infrared detectors is an infrared photoplethysmograph.

According to still further features in the described preferred embodiments said at least two infrared detectors include three detectors each independently being for collecting infrared spectral emission data from said region, said three detectors being positionable in a spaced apart configuration against said region of said skin.

According to still further features in the described preferred embodiments the at least one hemodynamic vascular parameter is selected from the group consisting of blood viscosity, blood density., a radius of said blood vessel, an elasticity of said blood vessel, systolic blood pressure, diastolic blood pressure and continuous blood pressure.

According to still further features in the described preferred embodiments said infrared spectral data is collected by each of said at least two infrared detectors over the course of at least one heart beat cycle.

According to still further features in the described preferred embodiments said infrared spectral data is continuously collected by each of said at least two infrared detectors, thus enabling continuous monitoring of the at least one hemodynamic vascular parameter.

According to still further features in the described preferred embodiments the system of claim 1, further comprising a device being for obstructing flow in said blood vessel down stream from said region of said skin.

According to still further features in the described preferred embodiments the system further comprising an interface communicating with said processing unit, said interface being for providing information pertaining to the at least one hemodynamic vascular parameter to an operator of the system.

According to still further features in the described preferred embodiments said information pertaining to the at least one hemodynamic vascular parameter is provided to said operator in at least one format selected from the group consisting of a textual format, a graphic format and an audio format.

According to still further features in the described preferred embodiments said processing unit implements an algorithm which serves to account for blood reflection waves resulting from reflection sites in blood vessels, so as to yield said information pertaining to the at least one hemodynamic vascular parameter of the individual.

According to still further features in the described preferred embodiments said algorithm calculates said information pertaining to the at least one hemodynamic vascular parameter of the individual by determining a wave propagation velocity, a reflection coefficient and a distance to a reflection site.

According to still further features in the described preferred embodiments said algorithm calculates said information pertaining to the at least one hemodynamic vascular parameter of the individual by extracting values pertaining to motion of a vessel wall under an assumption that a reflection coefficient is constant with respect to a frequency of a specific harmonic.

According to still further features in the described preferred embodiments said algorithm calculates said information pertaining to the at least one hemodynamic vascular parameter of the individual taking into account information pertaining to a foot to foot speed and calculating a wall displacement in order to calculate a forward propagating wave.

According to still further features in the described preferred embodiments said algorithm calculates said information pertaining to the at least one hemodynamic vascular parameter of the individual by extracting values pertaining to wall displacement and blood flow.

Implementation of the method and system non-invasively monitoring at least one hemodynamic vascular parameter of an individual or the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

The present invention successfully addresses the shortcomings of the presently known configurations by providing a system and method for monitoring hemodynamic vascular parameters in an easy continuous and accurate manner.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
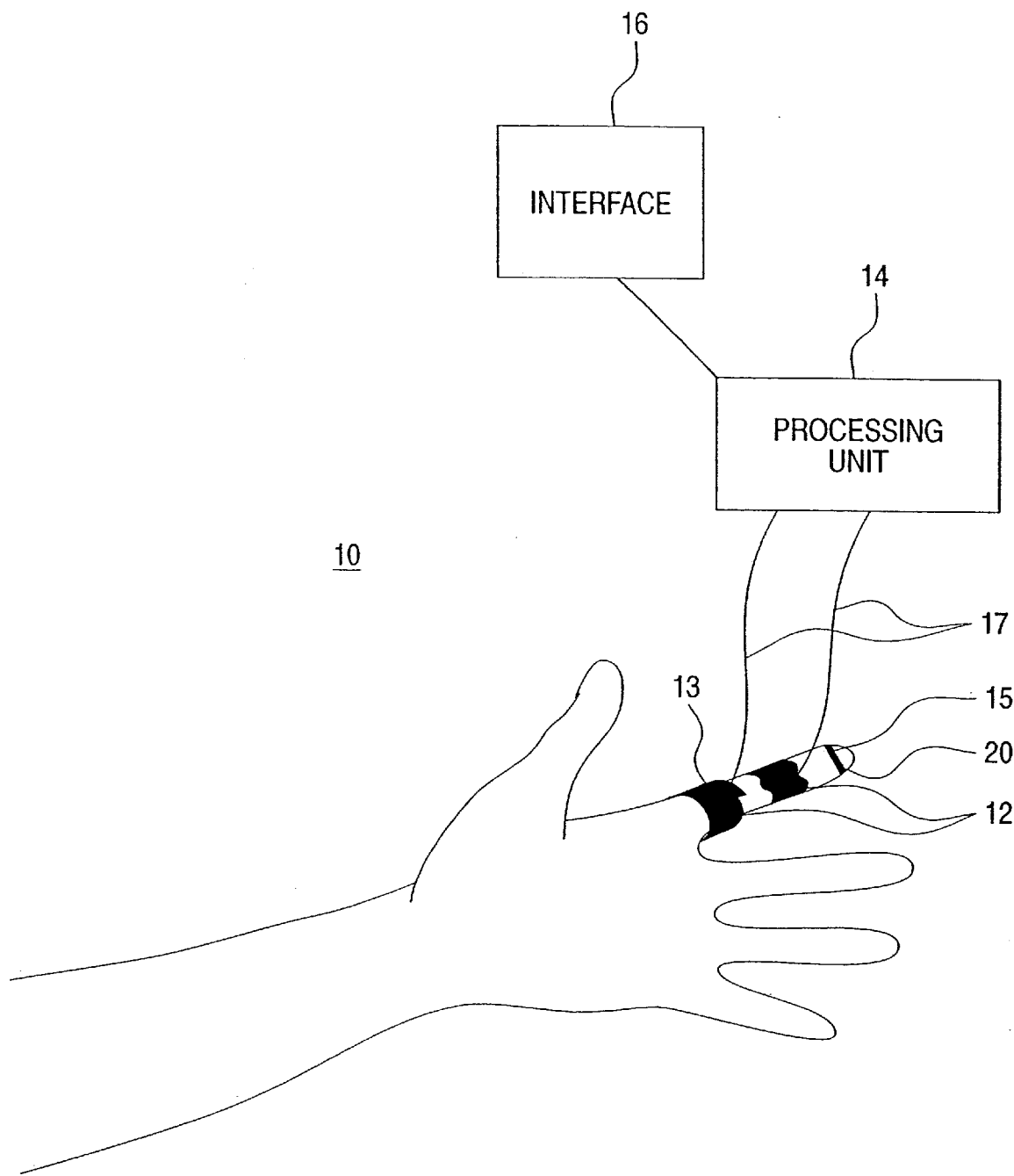
FIG. 1 is a drawing depicting the system of the present invention showing the placement of the detectors on a finger of an individual.

The present invention is of a system and method which can be used to non-invasively monitor at least one hemodynamic vascular parameter of an individual. Specifically, the present invention can be used to monitor a hemodynamic vascular parameter such as, for example, blood pressure in a continuous, non-invasive manner.

The principles and operation of a system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates the system of the present invention which is referred to herein under as system 10.

System 10 serves for non-invasively monitoring at least one hemodynamic vascular parameter of an individual. System 10 includes at least two infrared detectors 12 which are positionable in a spaced apart configuration against a region of a skin of the individual above at least one blood vessel. Preferably detectors 12 are positioned over a length of a single blood vessel, such as an artery, a vein or a set of capillaries.

According to a preferred embodiment of the present invention the blood vessel is an artery.

As specifically shown in FIG. 1, detectors 12 are preferably positioned on a finger of the individual, such as, for example, an index finger, via for example an adhesive surface or bindings, although positioning on other regions of the body, such as for example on an y of the foot tows, earlobe, etc., can also be realized by the present invention. Positioning detectors 12 on a finger is particularly advantageous since it substantially increases the chances that detectors 12 are co-positioned over the same group of blood vessels. In addition, blood vessels running through a finger are less branched and therefor less likely to contribute to wave reflections generated by vessel branching points (wave reflections are further described herein under and in the Examples section which follows).

Each of detectors 12 serves for individually collecting infrared spectral data from region of the skin. Detectors 12 are positioned along the length of the blood vessel, spaced apart, such that changes in for example a blood volume, or a volume of the blood vessel resultant from the propagation of a heart beat are sequentially detected by detectors 12, first by an upstream detector 13, followed by a downstream detector 15. Thus data collected by detector 15 will always be phase shifted from the data collected by detector 13, which phase shift is related to a distance between detectors 13 and 15.

Each detector 12 is preferably provided with an infrared irradiation source which irradiates infrared light of a wavelength within a range of 800 nm to 960 nm and a sensor for collecting reflected infrared radiation. Preferably detectors 12 are infrared photoplethysmograph detectors of which several examples are available commercially. For example TSD 100 photoelectric plethysmopram transducer (BIOPAC Systems, Inc.). The reflected infrared radiation collected by detectors 12 contains infrared spectral data which when analyzed is indicative of a state and amount of a blood volume present within the blood vessel.

System 10 of the present invention further includes a processing unit 14. The infrared spectral data collected by detectors 12 is translated into an electrical signal and relayed via wire connection (indicated by 17) to processing unit 14.

Processing unit 14 serves for independently processing infrared spectral data collected by each of detectors 12 to thereby yield information pertaining to at least one hemodynamic vascular parameter of the individual. It will be appreciated that the data collected by detectors 12 can be collected from a single heart beat cycle or from a plurality of heart beat cycles. It will further be appreciated that since data can be collected by detectors 12 continuously, monitoring of hemodynamic vascular parameters of an individual over a predetermined period of time covering several to numerous heart beat cycles can be effected by the system of the present invention.

The processed spectral data can yield information pertaining to several hemodynamic vascular parameters which are of clinical importance, these parameters include but are not limited to, blood viscosity, blood density, a radius of the blood vessel, an elasticity of the blood vessel, systolic blood pressure, diastolic blood pressure and continuous blood pressure which can independently or in combination be indicative of a physiological state of an individual.

Such processing is performed by dedicated algorithms executed by processing unit 14. An example to an algorithm for calculating the above parameters is further detailed in Example 1 of the Examples section.

System 10 further includes an interface communicating with processing unit, interface 16 which serves for providing information pertaining to a hemodynamic vascular parameter or parameters to an operator of system 10. Preferably interface 16 includes a display and operator control such that information pertaining to hemodynamic vascular parameters of an individual monitored are displayed in real time, on demand, in either a textual format, a graphic format or an audio format or any combination of these formats.

It will be appreciated that in order to yield accurate information pertaining to hemodynamic vascular parameters consideration must be given to the effect of reflection sites in the blood vessel caused by branching or obstructions. This effect has to be taken into account since the resultant information processed from the data collected by detectors 12 is a summation of the components with phase differences between the forward and the backward wave with respect to a reflection coefficient and a harmonic number. This effect and its consequences on the information extracted from the data collected by detectors 12 is further described in the Examples section which follows.

Several methods and/or system configuration can be implemented by the present invention in order to nullify the effect of reflection sites and phase differences.

According to one preferred embodiment of the present invention, system 10 of the present invention includes at least one additional detector (not shown) which is similar in function to detectors 12.

This three detector embodiment of system 10 is positioned in a spaced apart configuration against region of skin and is similar in function to the two detector embodiment described hereinabove other than the fact that three separate data collections are simultaneously effected. By comparing data from three detectors 12, the system of the present invention enables to take into account the effect caused by reflection sites. Further description to the advantages of a three detector configuration is given in Example 5 of the Examples section.

According to another preferred embodiment of the present invention system 10 includes an obstruction device 20 which is positionable downstream of detector 15 and serves to generate a single reflection site by constricting the blood vessel thus obstructing flow down stream of detector 15. Such a device can be, for example, a clamp or any device capable of obstructing blood flow.

An alternative and preferred method of solving the problem generated by reflection sites is to employ a dedicated algorithm when processing the data collected by detectors 12, which algorithm assumes the presence of one main reflection site beyond detector 15 and no major change in the blood vessel between the two detectors.

Thus according to a preferred embodiment of the present invention processing unit 14 implements an algorithm which serves to account for blood reflection waves resulting from reflection sites in blood vessels, so as to yield information pertaining to hemodynamic vascular parameter(s) of the individual.

According to one preferred embodiment of the present invention this algorithm takes into account a wave propagation velocity, a reflection coefficient and a distance to a reflection site. Further detail of this algorithm is given in Example 2 of the Examples section.

According to another preferred embodiment of the present invention this algorithm extracts values pertaining to monition of a vessel wall under an assumption that a reflection coefficient is constant with respect to a frequency of a specific harmonic. Further detail of this algorithm is given in Example 4 of the Examples section.

According to another preferred embodiment of the present invention this algorithm takes into account information pertaining to a foot to foot speed and calculating a wall displacement in order to calculate a forward propagating wave. Further detail of this algorithm is given in Example 6 of the Examples section.

According to another preferred embodiment of the present invention this algorithm extracts values pertaining to wall displacement and blood flow. Further detail of this algorithm is given in Example 7 of the Examples section.

Thus by implementing any of the above described algorithms system 10 of the present invention can provide information pertaining to hemodynamic vascular parameters such as for example blood pressure in an accurate and easy to obtain manner.

It will be appreciated that the hemodynamic information provided by interface 16 as described above is preferably provided in an accepted or commonly used measurement units, such as for example, indicating blood pressure values by mm Hg. To translate the information calculated from the data collected by detectors 12, pertaining to, for example, blood pressure, this information can be inputted into a lookup table maintained by processing unit 14 to thereby extract information in mm of Hg.

Alternatively, an initial calibration of system 10 against a reading taken by a prior art device, such as for example a FINAPRES system is effected, following which, information provided by system 10 is adjusted to standard or accepted units.

Alternatively, an intrinsic procedure can be initiated for calibration without a different device or a cuff embedded system, by applying an algorithm based on the computed parameters of blood vessels and photoplethysmograph devices.

While reducing the present invention to practice several results pertaining to hemodynamic vascular parameters were obtained and compared to those obtained by the FINAPRES system. These results, which are further detailed in Example 3, clearly show that the system of the present invention can provide real time continuous monitoring of hemodynamic vascular parameters while maintaining a high degree of accuracy.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Validation of Results

In order to evaluate the blood pressure (BP) results obtained by the system and method of the present invention, the FINAPRES system (Omeda) was used to perform a continuous BP measurement. The FINAPRES system is well accepted in the medical research community as a reliable device for continuous blood pressure measurement. The FINAPRES system measures continuous blood pressure using an inflatable cuff and a photoplethysmograph (or two cuffs in improved models).

The BP results obtained by the FINAPRES system were used to validate the results obtained by the system and method of the present invention.

Symbols Legend

The following symbols are used throughout Examples 1–6 of the Examples section.

| | |
|---|---|
| $\eta_{1n}$ | Wall displacement at the first detector |
| $\eta_{2n}$ | Wall displacement at the second detector |
| $\gamma_n$ | Reflection coefficient |
| $\alpha$ | Womersley variable |
| $\beta$ | Velocity frequency depended part |
| $v$ | Blood viscosity |
| n | Harmonic number |
| f | Frequency of the heart |
| L | Distance to the reflection point |
| l | Distance between the PPG detectors |
| R | Blood vessel radius |
| HR | Heart rate |
| $c_n$ | the forward propagated wave velocity of the $n^{th}$ harmonic |
| $\psi_n$ | Phase shift between the to detectors due to the forward propagated wave |
| E | Young modulus of elasticity |
| h | Blood vessel thickness |
| H | Effective Blood vessel thickness |
| $\rho$ | Blood vessel specific weight |
| $\rho_t$ | Specific weight of the tissue that surrounds the vessel |
| $\rho_w$ | Specific weight of blood vessel |
| K | Bulk elastic modulus |
| G | Lame coefficient |
| $\lambda$ | Wave length of the wall displacement |
| A | Constant of the solution to the wall displacement |
| $C_2$ | Constant of the solution to the wall displacement |
| $\omega$ | Radial velocity |
| p | Blood pressure in the vessel |
| r | Radius from the axis to the point of calculation |
| $\xi$ | Wall displacement in the longitudinal direction |
| $\eta$ | Wall displacement in the radial direction |
| u | Fluid velocity in the longitudinal direction |
| v | Fluid velocity in the radial direction |
| P | Pressure gradient in the longitudinal direction |
| $\epsilon$ | Strain pre unit of length |
| $\sigma$ | Stress pre unit of length |
| T | Radial tension |
| $\Delta P$ | Pulse pressure |
| V | Blood volume under the PPG detector |
| g | Electric gain of the detector |
| $v_{bias}$ | Electric bias of the detector |
| $\phi$ | Relation between the volume of blood and the vessel radius |

Example 1

General Outline of the Method of the Present Invention

The present invention utilizes two or more photoplethysmograph detectors to collect infrared signal data from blood vessels underlying the skin.

In order to process the signals resultant from the photoplethysmograph detectors (PPG detectors or PPGs) into values useful for determining parameters such as, for example, blood pressure, blood viscosity, blood density, blood vessel radius and blood vessel elasticity, the following general steps are performed.

(i) A low pass filter (~250 Hz) is used to remove noise from the signals generated by from the PPG detectors.

(ii) The beginning and end of a heart beat are detected by finding the local minimum points of the PPG signals.

(iii) The signals from each PPG detector are divided into separate segments, each segment being reflective of a single heart beat. Segments from the PPGs corresponding to the same heart beat are co-analyzed.

(iv) A fast Fourier transform (FFT) is performed for each segment of catch PPG signal in order to divide each heart beat into its spectral components, as these components are collected by the PPG detectors.

(v) The velocity of the forward propagating wave is calculated using the reflection coefficient and the distance to the reflection point for each spectral component (harmonic), of each heart beat as is further detailed hereinbelow.

(vi) The results for each heart beat are analyzed in order to detect any deviations in the calculated values which can be indicative of problems in the measurement or calculations, or of blood flow irregularities.

(vii) Blood vessel wall displacement and blood flow values are extracted using the values determined in step (v). Calculated velocities (obtained in step (v)) are used to extract the "effective" blood vessel Radius (R), and the elasticity of the vessel wall (E) or the pulse wave velocity, as is further detailed hereinbelow.

The beat to beat, systolic, diastolic and continuous blood pressure (entire waveform) can be determined using the above parameters as these are extracted from the PPG signals.

The accumulated data can then be processed, calibrated and displayed in, for example, mm Hg, thus enabling a physician to continuously track the blood pressure of an individual.

Detailed Description of the Method Steps

Figure 2:
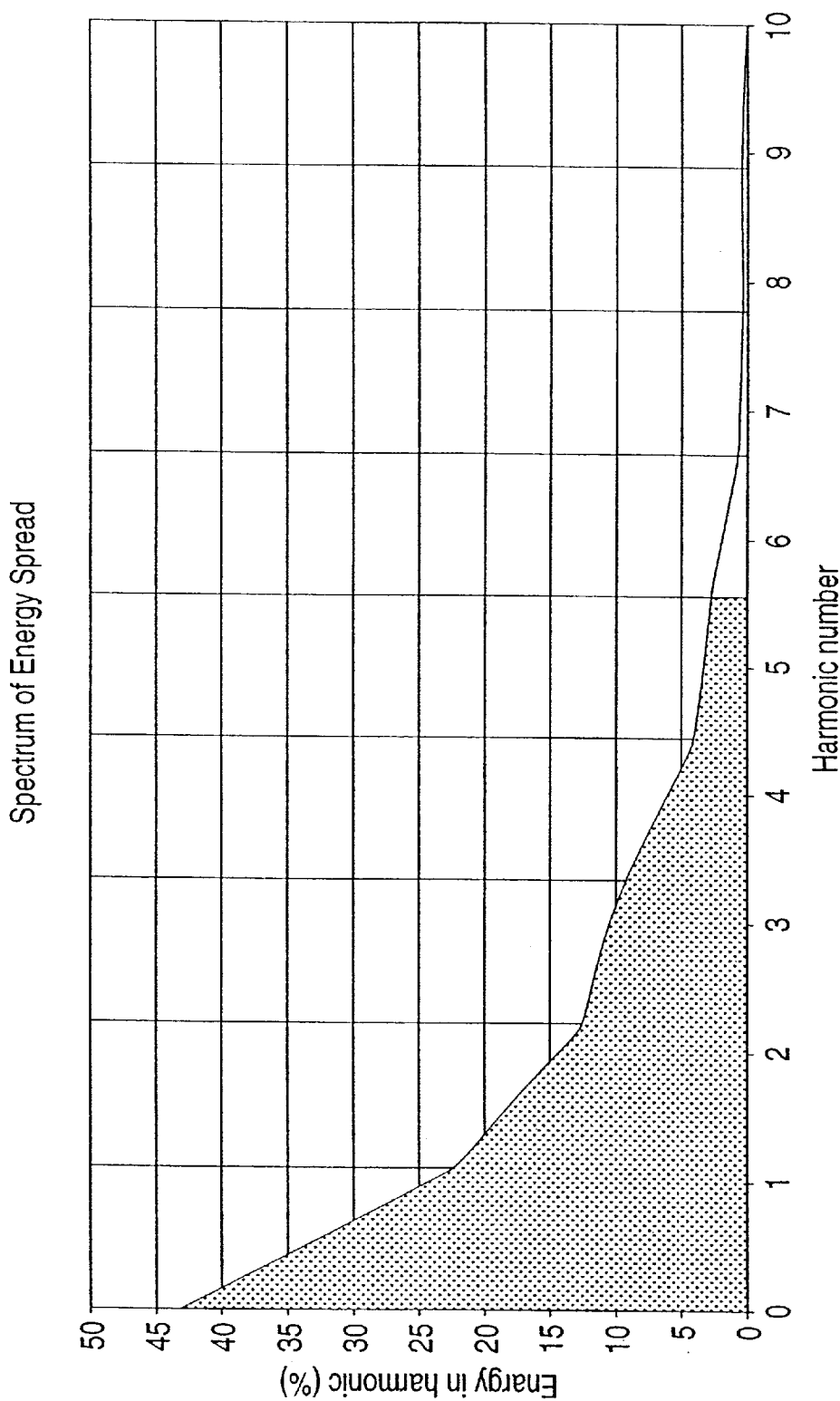
FIG. 2 is a graph displaying the energy content of a single heart beat as a function of the harmonic number.

Energy Content of a BP Wave:

As is clearly shown in FIG. 2, to implement the method according to the present invention measurements spanning 6 harmonics (n=6) or less (e.g., n=4) can be taken. This is due to the fact that the energy content in harmonics above n=6 is extremely low and thus less useful in subsequent calculations.

Thus, the system of the present invention extracts 6 harmonics from a heart beat measurement in order to obtain the velocity spectrum, although it will be appreciated that as few as, for example, 4 harmonics are sufficient to obtain the blood vessel parameters described hereinabove.

One of the major problems in measuring BP with PPG detectors is calculating the forward propagating wave velocity.

Figure 3:
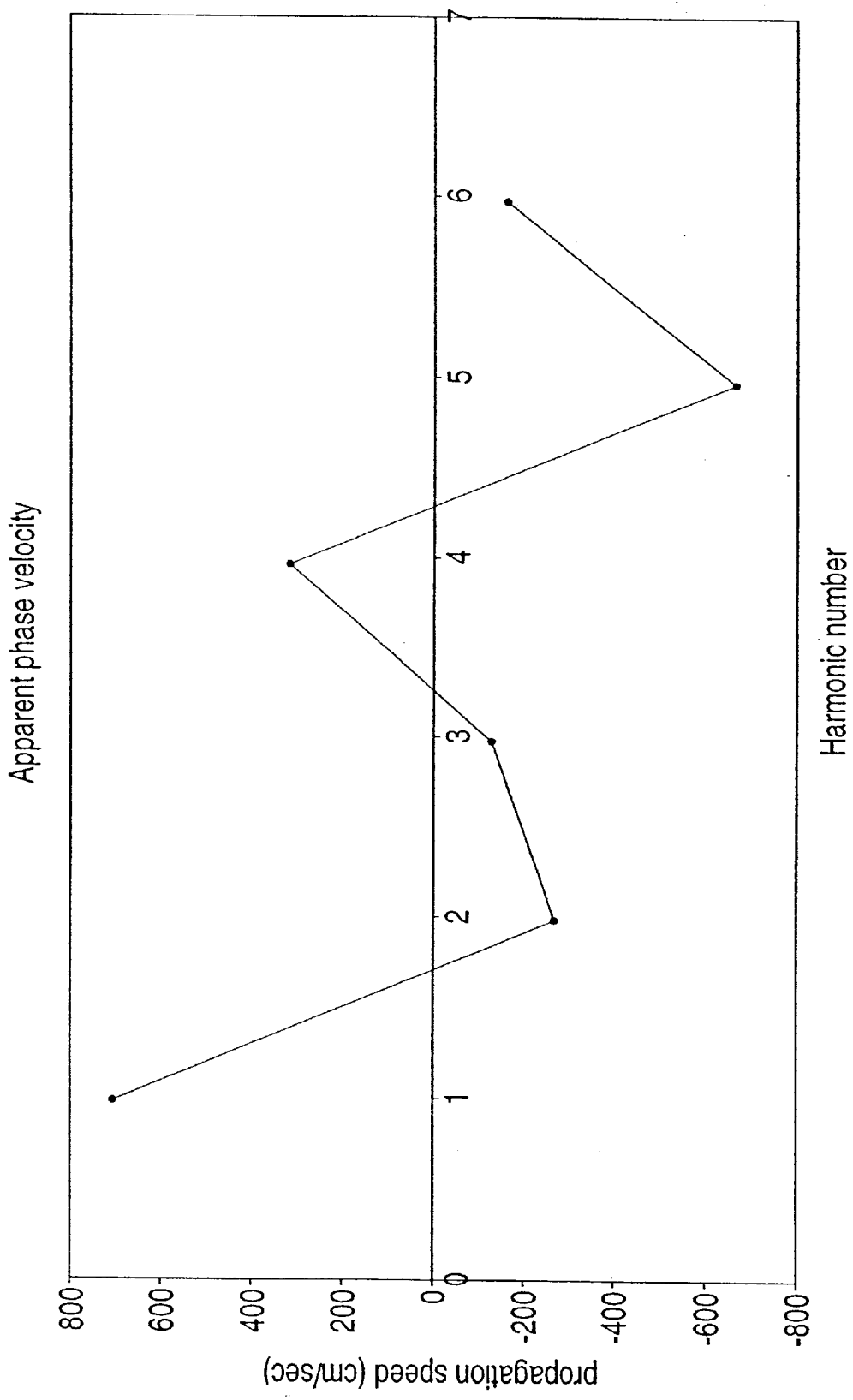
FIG. 3 is a graph displaying pulsewave velocity, as obtained by a direct measurement approach.

A direct pulse wave measurement approach failed to achieve the desired results (as shown in FIG. 3). The main reason to this failure was the fact that the direct method does not take into consideration the effect of the reflection sites in blood vessel branching. The result that is obtained by the direct method is a summation of the phase differences between the forward and the backward wave with respect to the reflection coefficient and the harmonic number.

Figure 4:
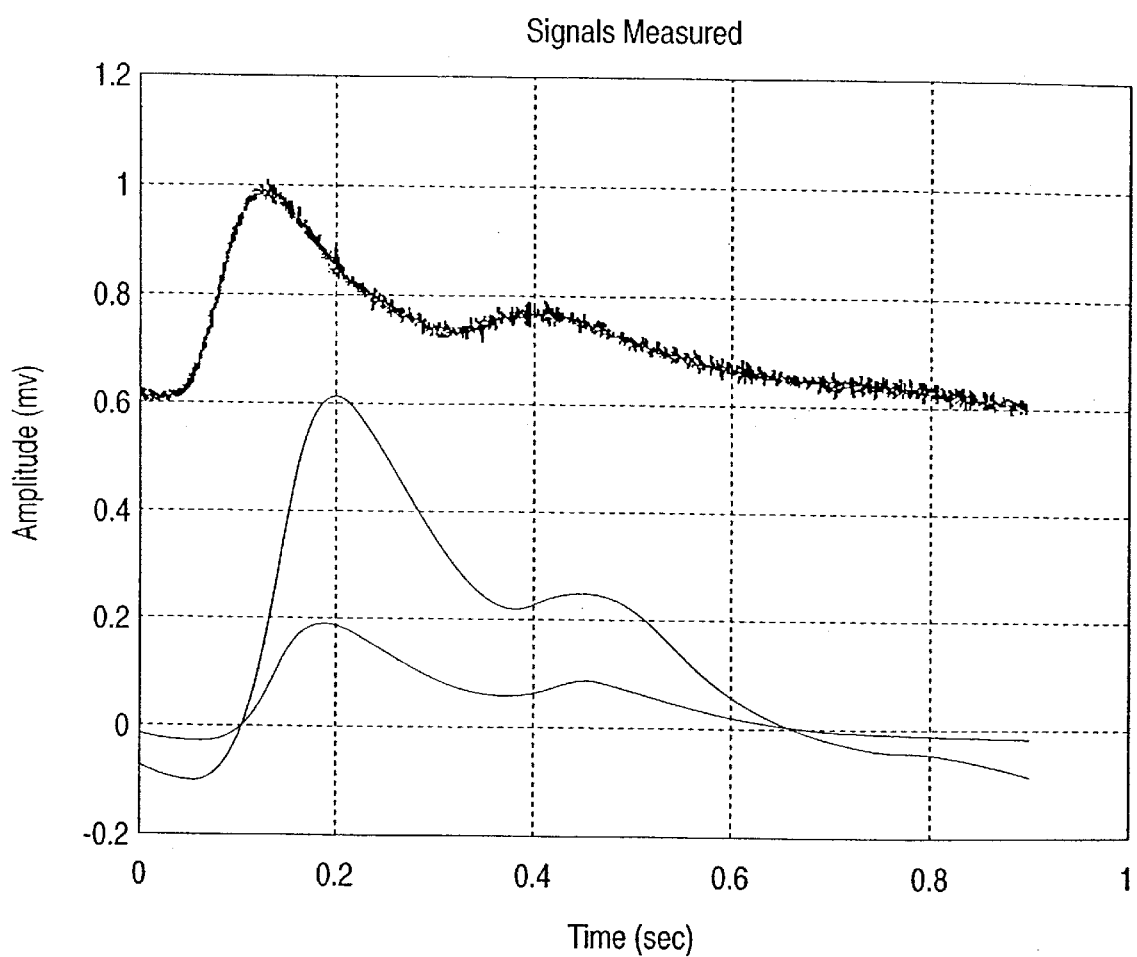
FIG. 4 is a graph displaying data collected by the detectors of the system of the present invention as compared to data collected by the FINAPRES system.

In order to solve this problem, a proposed algorithm of the present invention assumes the presence of one main reflection site beyond a second PPG (of two PPGs utilized) and no major change in the blood vessel between the two detectors themselves. In addition, it is also possible to create a thin blood layer occlusion site in a blood vessel by artificially occluding the blood vessel behind the second detector thus creating one main reflection site. FIG. 4 represents signals measured by a two detector configuration of the system of the present invention as is compared to a signal measured by the FINAPRES system.

Several methods and system configurations can be implemented by the present invention in order to solve the problems associated with reflection.

(i) Iterative calculation over the wave propagation velocity, reflection coefficient and the distance to the reflection point, collectively termed as IRC. This method is further detailed hereinbelow under Example 2.

(ii) Extracting values pertaining to motion of a vessel wall under the assumption that the reflection coefficient is constant with respect to the frequency of the harmonic number. This method is further detailed hereinbelow under Example 4.

(iii) Using three equally spaced apart PPG detectors in order to cancel out the reflected wave while calculating the forward propagating wave velocity. This method is further detailed hereinbelow under Example 5.

(iv) Measuring the foot to foot speed and solving the Equation of the wall displacement in order to calculate the forward propagating wave. In this method the foot to foot speed is obtained as an approximation to the forward wave velocity for the fifth harmonic. From the fifth harmonic the distance to the reflection point is obtained and then used to solve the other harmonics. This method is further detailed hereinbelow under Example 6.

(v) Calculating both the flow and the wall displacement from the signal obtained by the PPG detectors and then extracting values for the wall displacement (pressure) and blood flow. This method processes the PPG signal with respect to time and flow, and by using the impedance of the blood vessel the forward propagated wave and the backward propagated wave can then be obtained. This method is further detailed hereinbelow under Example 7.

Preferably, the system and method of the present invention implement the IRC method.

Example 2

The IRC Method

The following Equations are utilized in order to determine parameters associated with blood flow in a blood vessel according to preferred embodiments of the present invention.

Figure 5:
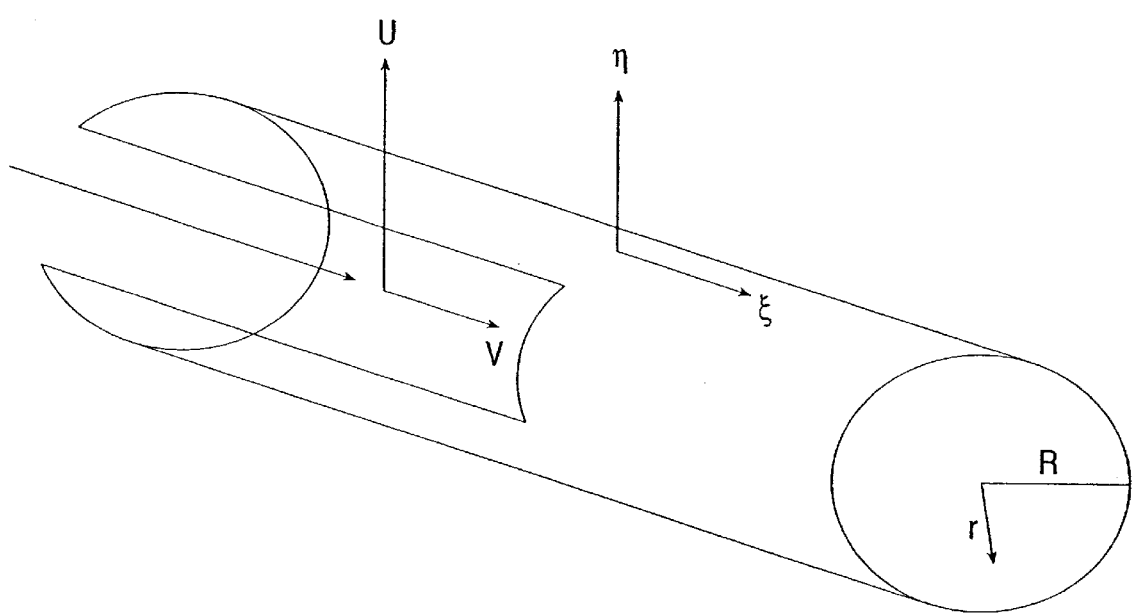
FIG. 5 is a perspective drawing of a model of a blood vessel.

A model of a blood vessel is represented in FIG. 5.

The following Equations describe the amplitude of the blood volume signals ($\eta_1$, $\eta_2$) measured by the two PPG detectors, as a function of the forward wave amplitude ($A_n$).

In all the Equations below n indicates the harmonic number. Each of the Equation is then used for n=1 . . . 6.

$$\eta_{1n} = A_n(1 + \gamma_n e^{-i\psi_n(2L_n+2l)}) \quad (1)$$

$$\eta_{2n} = A_n(e^{-i\psi_n l} + \gamma_n e^{-i\psi_n(2L_n+l)})$$

The above pair of Equations can be reduced to a single Equation without the dependence on the forward wave amplitude ($A_n$):

$$\frac{\eta_{1n}}{\eta_{2n}} = \frac{1 + \gamma_n e^{-i\psi_n(2L_n+2l)}}{e^{-i\psi_n l} + \gamma_n e^{-i\psi_n(2L_n+l)}} \quad (2)$$

Equation 2 can be rearranged in order to reflect the dependence on $$\gamma_n e^{-i\psi_n(2L_n+l)} = \frac{\eta_{2n} - \eta_{1n} e^{-i\psi_n l}}{\eta_{1n} - \eta_{2n} e^{-i\psi_n l}} \quad (3)$$

The reflection coefficient can be described by the following Equation (4) assuming that $\gamma_n$ has only a real value:

$$\gamma_n = \left| \frac{\eta_{1n} \cdot e^{i\psi_n l} - \eta_{2n}}{\eta_{2n} \cdot e^{i\psi_n l} - \eta_{1n}} \right| \quad (4)$$

Due to the fact that the phase difference between the forward propagated wave on the two detectors is small, one can approximate the following:

$$e^{-i\psi_n(2L_n+l)} = 1 - i(2L_n+l)\psi_n \quad (5)$$

$$e^{-i\psi_n l} = 1 - i\psi_n l$$

The above are first order approximations, yet because the Equations are solved by a recursive method, and due to the values expected for the phase velocity, this approximation is sufficient.

Applying these approximations, the following Equation (6) is obtained:

$$\gamma_n(1 - i\psi_n(2L_n+l)) = \frac{\eta_{2n} - \eta_{1n}(1 - i\psi_n l)}{\eta_{1n} - \eta_{2n}(1 - i\psi_n l)} \quad (6)$$

Solving Equation 6 for the propagation velocity, the following expression is obtained:

$$\psi_n^2 \gamma_n \eta_{2n} l(2L_n+l) + \ldots - i\psi_n(\eta_{1n}(1+\gamma_n(2L_n+l)) - 2\gamma_n \eta_{2n}(L_n+l)) + \ldots + (\eta_{1n} - \eta_{2n})(\gamma_n+1) = 0 \quad (7)$$

Assuming that the propagation velocity, $\psi_n$, is known, the distance to the reflection point can be calculated by using the following Equation:

$$L_n = \text{Real}\left(-\frac{i}{4\gamma_n \psi_n}\eta_{2n} - \frac{\eta_{1n} \cdot (1+il\psi_n)}{\eta_{1n} - \eta_{2n} \cdot (1+il\psi_n)} + \frac{i}{4\psi_n} - \frac{l}{2}\right) \quad (8)$$

The following Equation can be utilized in order to evaluate the wall displacement wave velocity:

$$C_n = \frac{2\pi \cdot HR \cdot n}{60 \cdot \psi_n} \quad (9)$$

wherein HR is the heart rate (beats/minute), n is the number of the harmonic, and $\psi_n$ is the forward wave phase velocity (rad/cm).

Figure 6:
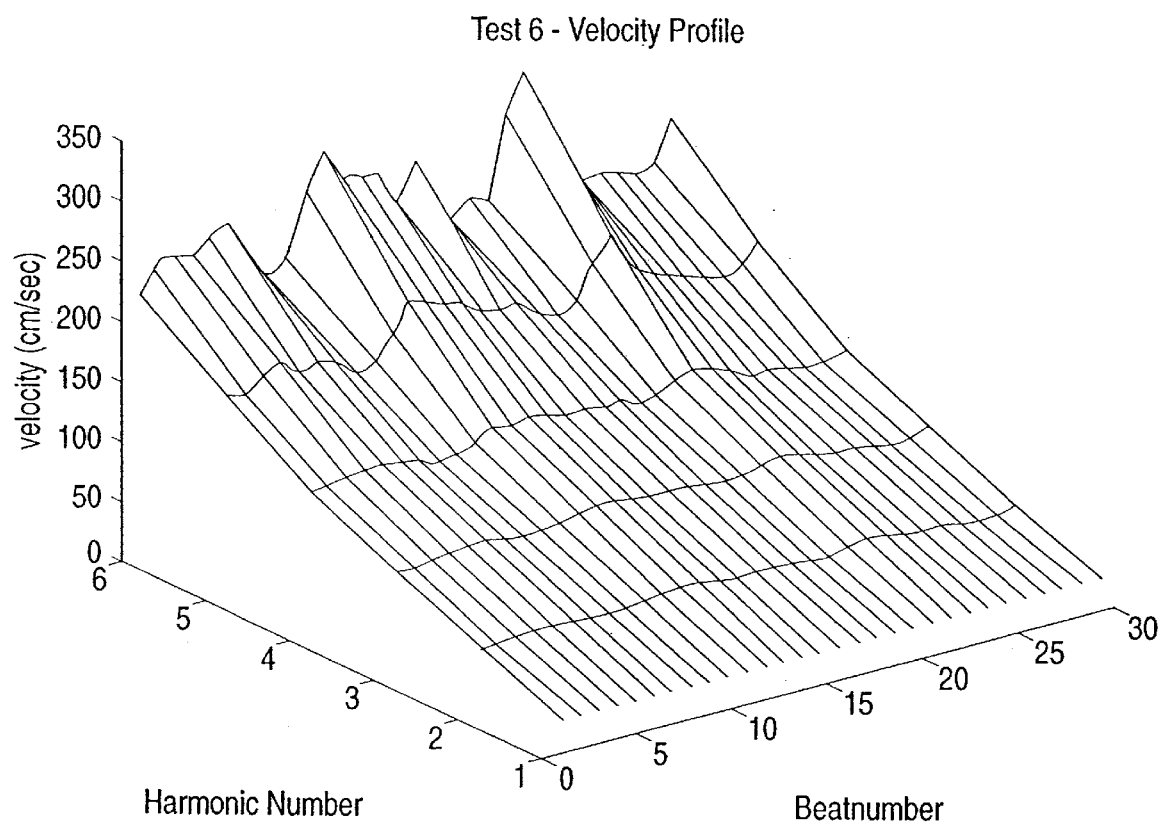
FIG. 6 is a three dimensional graph displaying a velocity spectrum obtained by the system of the present invention.
Figure 7:
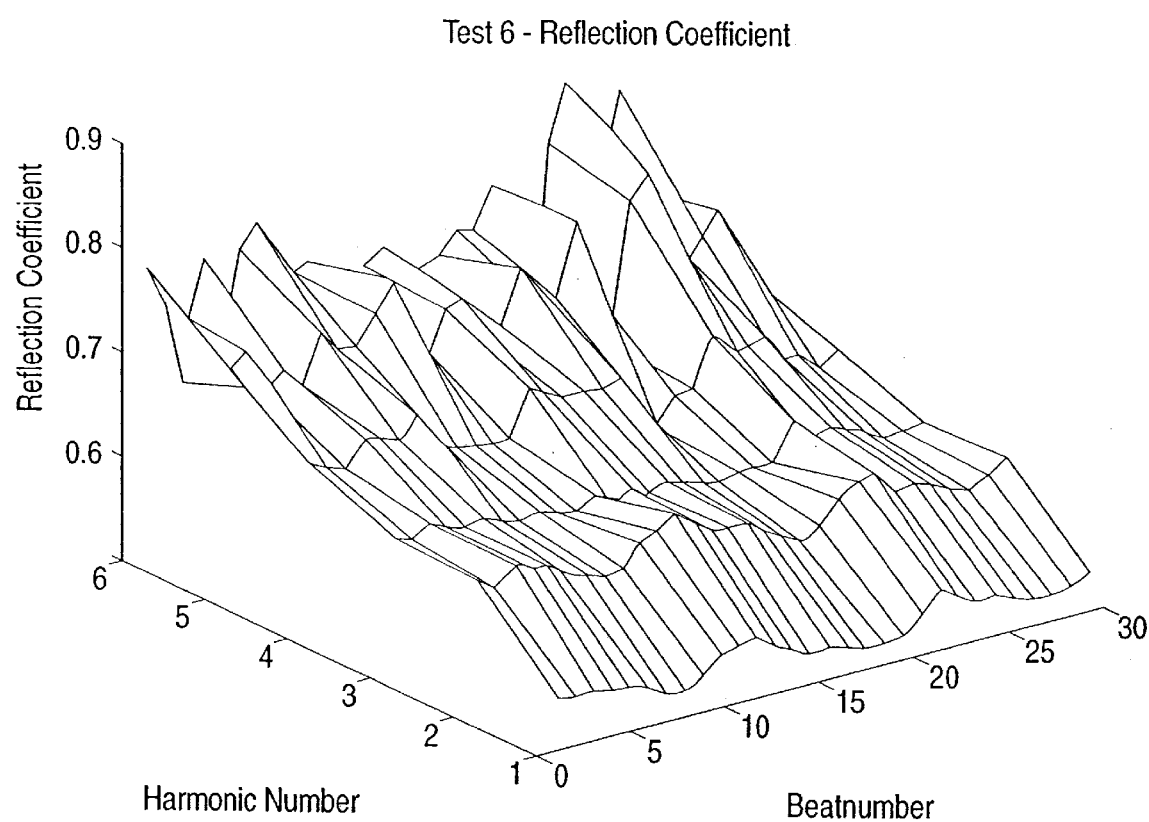
FIG. 7 is a is a three dimensional graph displaying a reflection coefficient profile as obtained by the system of the present invention.

The resulting $C_n$ value is the wall displacement wave velocity (cm/sec) for each spectral component of the forward propagated wave. A 3D profile showing a velocity spectrum calculated as described hereinabove is presented in FIG. 6, a reflection coefficient profile calculated according to the present invention is presented in FIG. 7.

Calculating Blood Vessel Parameters:

By inputting the measured velocities into Equations detailing blood flow in a symmetrical tube such as shown in FIG. 5, parameters for the "effective" blood vessel can be calculated The frequency dependent parameter $$\beta = R \cdot \sqrt{\frac{2\pi f}{v}} \quad (10)$$

is used to obtain R, the "effective" radius of the blood vessel, under the assumption that v, the blood viscosity, is known, whereas f is the heart rate frequency.

By using the DC component of the signal in order to independently measure the radius of the blood vessel, R, and while partially correlating it with β, one can measure the blood viscosity, ν.

The elasticity of the blood vessel, E, is calculated using the true phase velocity of the wall displacement wave, $C_0$, assuming that the ratio HIR (thickness of blood vessel wall over radius of the vessel) is known.

To achieve these goals, one has to apply Equations pertaining to flow in cylindrical vessels, such as that shown in FIG. 5. Blood flow in a cylindrical tube was first described by Womersley ("cardiovascular fluid dynamics"—Uri Dinnar, CRC Press, 1981, and "The fluid mechanics of large blood vessels",—T. J. Pedley, Cambridge University Press, 1980.

The following Equations describe the flow of a fluid inside a symmetrical tube (see FIG. 5), both in the radial and the longitudinal directions.

Flow in the longitudinal direction is described by:

$$\frac{\partial v}{\partial t} = -\frac{1}{\rho}\frac{\partial p}{\partial r} + \nu\left(\frac{\partial^2 v}{\partial r^2} + \frac{1}{r}\frac{\partial v}{\partial r} - \frac{v}{r^2}\right) \quad (11)$$

whereas, in the radial direction it is described by:

$$\frac{\partial u}{\partial t} = -\frac{1}{\rho}\frac{\partial p}{\partial z} + \nu\left(\frac{\partial^2 u}{\partial r^2} + \frac{1}{r}\frac{\partial u}{\partial r}\right) \quad (12)$$

Flow continuity is described by:

$$\frac{1}{r}\frac{\partial}{\partial r}(rv) + \frac{\partial u}{\partial z} = 0 \quad (13)$$

To solve the above Equations, the following variables are used in order to transform the Equations into dimensionless Equations:

$$\alpha^2 = R^2 \cdot \frac{\omega}{\nu}, \quad y = \frac{r}{R} \quad (14)$$

wherein R is the radius of the blood vessel, r is the radial distance from the symmetrical axis of the vessel, ν is the viscosity of the fluid and ω is angular velocity displacement of the proper harmonic.

When dealing with wave propagation, one can assume that all the variables have a similar wave like behavior as follows:

$$p(z,r,t)=P_0(r)e^{i\omega(t-z/c)} u(z,r,t)=V_0(r)e^{i\omega(t-z/c)} v(z,r,t)=U_0(r)e^{i\omega(t-z/c)} \quad (15)$$

After applying the extracted values and variables to the flow Equations, blood velocity inside the vessel can be obtained as follows:

In the longitudinal direction:

$$V_0(y) = i\frac{\omega R}{2c}\left(c_2 \frac{2J_1(i^{3/2}\alpha y)}{i^{3/2}\alpha J_0(i^{3/2}\alpha)} + A\frac{y}{\rho c}\right) \quad (16)$$

In the radial direction:

$$U_0(y) = c_2 \frac{J_0(i^{3/2}\alpha y)}{J_0(i^{3/2}\alpha)} + A\frac{1}{\rho c} \quad (17)$$

Using Equations 16 and 17 the blood flow within the vessel can be resolved. However, due to the fact that there is a displacement in the vessel wall, the boundary conditions that determine the value for the two constants, (A, $c_2$), are the continuity in the velocity of the fluid, the wall velocity at the meeting point, and forces that are applied at that point.

Thus, in order to find the values for A, $c_2$ one has to solve the Equations describing the wall displacement as well.

The following Equations describe the displacement of the vessel wall:

$$\rho_w \frac{\partial^2 v_r}{\partial t^2} = (G+\lambda)\frac{\partial}{\partial r}(\nabla \cdot \vec{v}) + G\left(\frac{\partial^2 v_r}{\partial r^2} + \frac{1}{r}\frac{\partial v_r}{\partial r} - \frac{v_r}{r^2} + \frac{\partial^2 v_r}{\partial z^2}\right) \quad (18)$$

$$\rho_w \frac{\partial^2 v_z}{\partial t^2} = (G+\lambda)\frac{\partial}{\partial z}(\nabla \cdot \vec{v}) + G\left(\frac{\partial^2 v_z}{\partial r^2} + \frac{1}{r}\frac{\partial v_z}{\partial r} + \frac{\partial^2 v_z}{\partial z^2}\right)$$

Assuming that the vessel wall is thin and the ratio of the lo wavelength over the radius of the vessel is large (λ>>R), one can calculate the strain by a simple balance of the forces applied to the vessel wall.

The following Equations describe the wall displacement of a blood vessel.

The radial displacement is described by:

$$\rho_w h \frac{\partial^2 \eta}{\partial t^2} = P(z,t) - \frac{Eh}{R(1-\nu^2)}\left(\frac{\eta}{R} + \nu\frac{\partial \xi}{\partial z}\right) \quad (19)$$

The longitudinal displacement is described by:

$$\rho_w h \frac{\partial^2 \xi}{\partial t^2} = \frac{Eh}{(1-\nu^2)}\left(\frac{\nu}{R}\cdot\frac{\partial \eta}{\partial z} + \frac{\partial^2 \xi}{\partial z^2}\right) - \mu\left(\frac{\partial u}{\partial r}\right)_{wall} \quad (20)$$

The moment of inertia, t, of the tissue that surrounds the vessel can be taken into consideration by assuming an effective wall thickness as is described by the following:

$$H = h + \frac{\rho_t R_1}{\rho_w R} \quad (21)$$

wherein $R_1$ is the thickness of the tissue and $\rho_t$ is the specific weight of the tissue.

The tissue also affects the ability of the vessel to move in the longitudinal direction (K in the following Equation). Thus Equation (20) can be extended to:

$$\rho_w H \frac{\partial^2 \xi}{\partial t^2} = \frac{EH}{(1-\nu^2)}\left(\frac{\nu}{R}\cdot\frac{\partial \eta}{\partial z} + \frac{\partial^2 \xi}{\partial z^2}\right) - \mu\left.\frac{\partial u}{\partial r}\right|_{wall} - K\xi \quad (22)$$

By using the following variables:

$$F_{10} = \frac{2J_1(i^{3/2}\alpha)}{i^{3/2}\alpha \cdot J_0(i^{3/2}\alpha)}, \quad B = \frac{E}{1-\nu^2}, \quad \alpha^2 = \frac{R^2\omega}{\nu}, \quad (23)$$

the Equation system can be solved by the following matrix:

$$\begin{vmatrix} 1 & \frac{1}{\rho c} & -i\omega & 0 \\ F_{10}\frac{i\omega R}{2c} & \frac{i\omega R}{2\rho c^2} & 0 & -i\omega \\ 0 & 1 & \frac{i\omega BHv}{cR} & \rho_w H\omega^2 - \frac{BH}{R^2} \\ F_{10}\frac{i\omega\rho R}{2} & 0 & \rho_w H\omega^2 - \frac{\omega^2}{c^2}BH - K & \frac{i\omega BHv}{cR} \end{vmatrix} = 0 \quad (24)$$

Due to the fact that the surrounding tissue of the vessel is connected to the body, one can assume that $K \to \infty$. The value represented by Equation (24) can then be represented by:

$$c^2 = R\left(\rho_w H\omega^2 - \frac{BH}{R^2}\right)\frac{(F_{10}-1)}{2\rho}. \quad (25)$$

Using the approximation $$\rho_w H\omega^2 \ll \frac{BH}{R^2}, \quad (26)$$

the following Equation, describing the wave propagation is obtained:

$$c^2 = \frac{EH}{2\rho R}\left[1 - \frac{F_{10}}{1-v^2}\right] \quad (27)$$

The value $C_0$ can now be used as the basic velocity of the wave and inputted into the following Equation:

$$c^2 = C_0(1 - F_{10}). \quad (28)$$

After obtaining the theoretical velocities using the IRC algorithm, one can fit these velocities to an analytical solution. While executing this process, one obtains a value for $EH/2R\rho(1-v^2)$ and a value for the frequency dependent $(1-F_{10})$.

Example 3

Results

Figure 8:
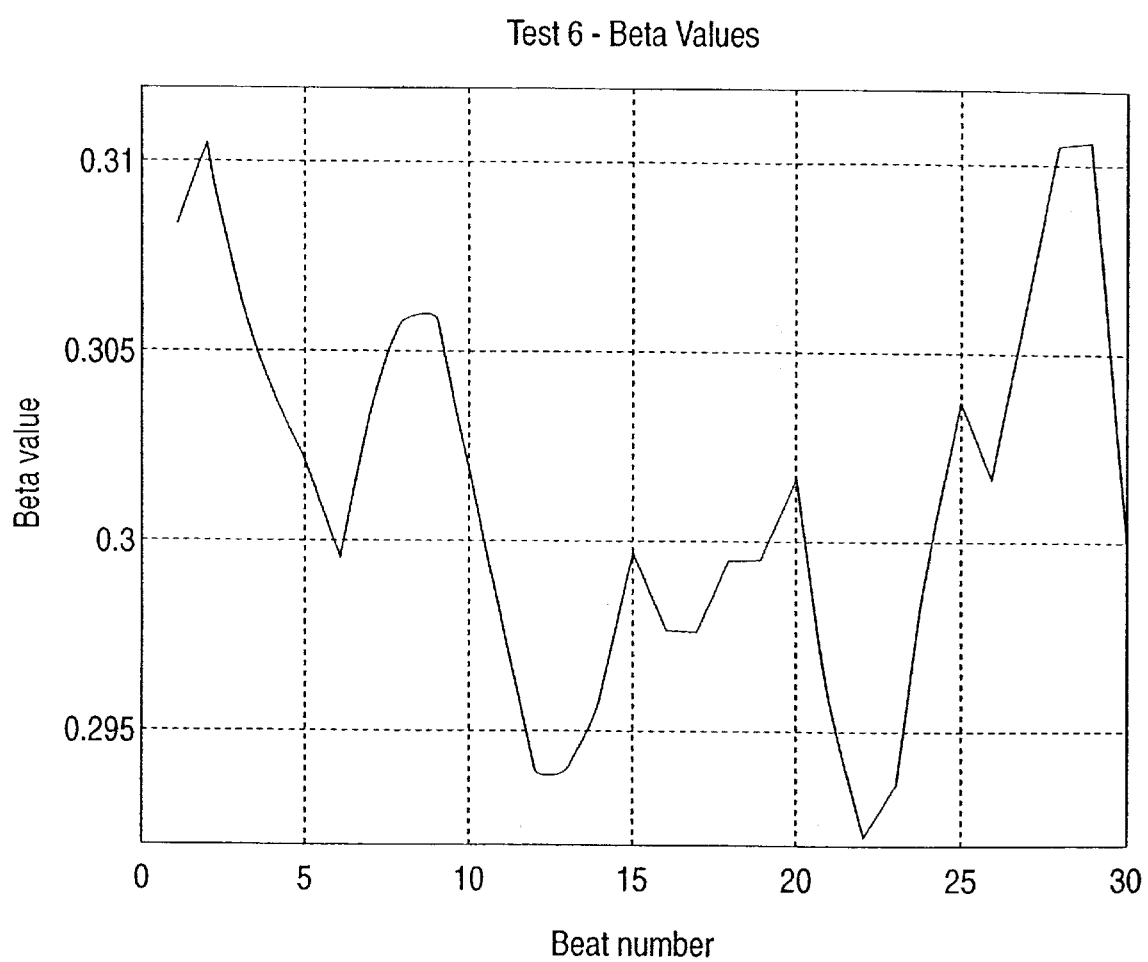
FIG. 8 is a graph displaying values for the beta variable obtained by the system of the present invention; note that the dynamic range of the values of beta is 0.02.
Figure 9:
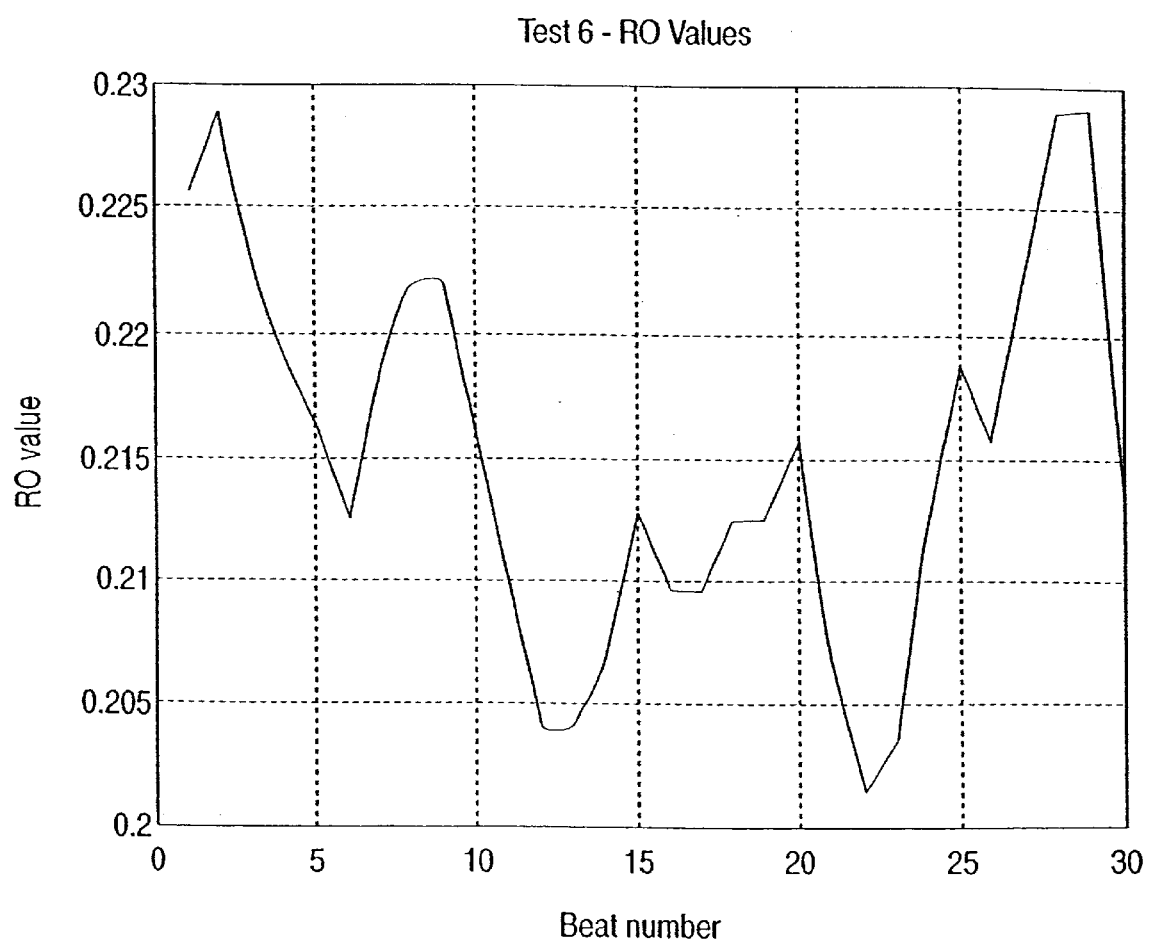
FIG. 9 is a graph displaying the values for the radius of the vessel when relaxed, obtained by the system of the present invention.
Figure 10:
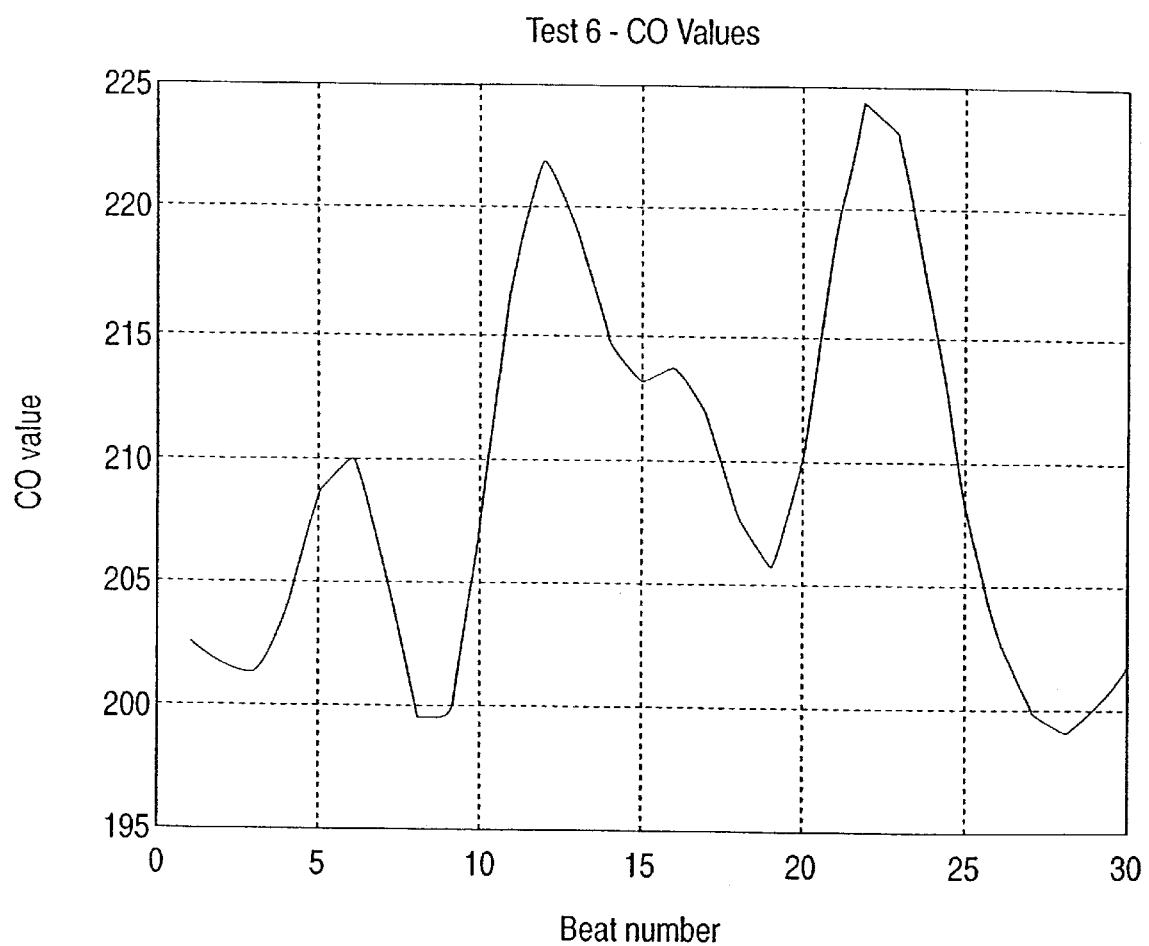
FIG. 10 is a graph displaying the values for the forward propagated wave velocity as obtained by the system of the present invention, note that these results are not calibrated.

Calculating R, β, $C_0$:

Table 1, and FIGS. 8–10 respectively, represent the results obtained for R, β, $C_0$ using the Equations described under Example 2. The values for $C_0$ were obtained prior to a calibration process and therefor are accurate only within a linear range of $C_0$. The values for R were calculated while assuming a known value for v (for blood, v=0.0381 cm²/sec) and are presented only to show the correlation with vivo measurements.

TABLE 1

| Test Number | Subject | $C_0$ (cm/sec) | β | R(cm) |
|---|---|---|---|---|
| 1 | G | 171 ± 6 | 0.325 ± 0.006 | 0.233 ± 0.008 |
| 2 | G | 185 ± 11 | 0.321 ± 0.007 | 0.226 ± 0.001 |
| 3 | E | 150 ± 4 | 0.333 ± 0.005 | 0.244 ± 0.007 |
| 4 | E | 151 ± 3 | 0.339 ± 0.005 | 0.252 ± 0.007 |
| 5 | A | 164 ± 10 | 0.324 ± 0.009 | 0.231 ± 0.013 |
| 6 | A | 196 ± 9 | 0.307 ± 0.008 | 0.207 ± 0.011 |
| 7 | A | 152 ± 9 | 0.328 ± 0.011 | 0.237 ± 0.015 |
| 8 | A | 194 ± 16 | 0.300 ± 0.014 | 0.198 ± 0.018 |

TABLE 1-continued

| Test Number | Subject | $C_0$ (cm/sec) | β | R(cm) |
|---|---|---|---|---|
| 9 | G | 185 ± 11 | 0.321 ± 0.007 | 0.226 ± 0.010 |
| 10 | G | 171 ± 6 | 0.325 ± 0.007 | 0.233 ± 0.008 |
| 11 | G | 164 ± 10 | 0.324 ± 0.009 | 0.231 ± 0.013 |
| 12 | A | 149 ± 29 | 0.335 ± 0.029 | 0.248 ± 0.041 |
| 13 | J | 136 ± 4 | 0.351 ± 0.005 | 0.270 ± 0.008 |
| 14 | J | 132 ± 2 | 0.354 ± 0.001 | 0.276 ± 0.001 |
| 15 | J | 141 ± 3 | 0.354 ± 0.001 | 0.275 ± 0.002 |
| 16 | O | 142 ± 3 | 0.354 ± 0.002 | 0.275 ± 0.002 |

Calculating a Continuous Blood Pressure:

Calculating a continuous blood pressure requires calculating the systolic and diastolic blood pressure and calculating the waveform of the continuous blood pressure signal.

Calculating the systolic and diastolic blood pressure for each heart beat can be achieved by using the Hill Equation ("cardiovascular fluid dynamics"—Uri Dinnar, CRC Press, 1981) and further by assuming (i) that in a blood vessel there is a linear correlation between stress and strain ($\sigma = E\cdot\epsilon$); (ii) that the fluid is uncompressed; and (iii) that the Poisson ratio equals 0.5. Thus, the following Equation for the strain of the blood vessel can be used when the radius of the vessel changes from R to R+η:

$$\varepsilon = \frac{2\pi(R+\eta) - 2\pi R}{2\pi R} = \frac{\eta}{R} \quad (29)$$

The radial tension, T, can be represented as a product of the stress (σ) per unit of length and the thickness of the vessel wall (h):

$$T = \sigma \cdot h = E \cdot h \cdot \frac{\eta(x,t)}{R} \quad (30)$$

The tension per unit length must be equal to the pressure applied by the fluid and its momentum. θ is the angle between the direction of the force and the vessel wall. These parameters are represented by the following:

$$\frac{Eh \cdot \sin(\theta)}{R}\eta = R\theta P - \rho_w h\ddot{\eta}R\theta \quad (31)$$

Using the approximation sin (θ)=θ, one obtains the following Equation describing the pressure within the blood vessel:

$$P = \frac{Eh}{R^2}\eta + \rho_w h\ddot{\eta} \quad (32)$$

The second half of the right side of Equation 32 can be ignored due to its size relative to the first half thereof, such that the pressure can be represented by the following proximation:

$$P = \frac{Eh}{R^2}\eta \quad (33)$$

A pressure difference between the systole and the diastole can be described by:

$$\Delta P = \frac{Eh}{R^2}(\eta_s - \eta_d) \tag{34}$$

wherein the vessel radius at the systole is represented by $\eta_s$ and the vessel radius at the diastole is represented by $\eta_d$.

Using the relation $$C_0^2 = \frac{Eh}{2\rho R},$$

in Equation 34 one obtains the following Equation; representing a pressure differential:

$$\Delta P = \frac{2\rho C_0^2}{R}(\eta_s - \eta_d) \tag{35}$$

wherein $C_0$ is the wave propagation velocity of the blood vessel wall displacement.

One can also calculate the wave velocity by using the Hill Equation:

$$C_0^2 = \frac{v}{\rho} \cdot \frac{\partial P}{\partial v} \tag{36}$$

from which the following is obtained:

$$\partial p = \rho C_0^2 \frac{\partial v}{v} \tag{37}$$

By integrating the diastolic point and the systolic point, a pressure difference between the systole and diastole can be obtained, which is equal to the pulse pressure ($\Delta P$):

$$\Delta P = P_s - P_d = \rho C_0^2 \ln\left(\frac{v_s}{v_d}\right) \tag{38}$$

The relation between the blood volume detected by the PPG detectors and the electrical output of the PPG detectors as a function of detector gain is given by the following Equation:

$$v_{out} = g(V + v_{bias}) \tag{39}$$

The following Equation describes the relation between the blood volume and the vessel radius:

$$V = \pi \epsilon \lambda R^2 \tag{40}$$

By substituting Equation 38 into Equation 36 and Equation 33, one can obtain the following relations for the pulse pressure:

$$\Delta P = P_s - P_d = \rho C_0^2 \ln\left(\frac{\frac{v_s}{g} - \varepsilon_{bais}}{\frac{v_d}{g} - \varepsilon_{bais}}\right) \tag{41}$$

$$\Delta P = \frac{\rho C_0^2}{2R\sqrt{\pi\epsilon\lambda\rho^4}}\left(\sqrt{\frac{v_s}{g} - v_{bias}} - \sqrt{\frac{v_d}{g} - v_{bias}}\right) \tag{42}$$

A partial correlation between beats and Equations 41 and 42 can be used in order to find the values of g, $v_{bias}$ and $\pi\lambda\epsilon\rho^4$. The resultant values can be calibrated against measurements taken with a simple cuff.

The values for $\beta$ and $C_0$ obtained from the Equations above and the DC component of the signal can be used to obtain R, by using the following Equation:

$$R = \sqrt{\frac{DC}{\pi\varepsilon\lambda}} \tag{43}$$

From the above calculated values, the blood vessel parameters v, $\rho$ and HE can be extracted. A calibration to a cuff measurement can be used to correlate Equations 41 and 43 to values measured for a number of heart beats.

Using these Equations in processing signals obtained by the PPG detectors described by the present invention enables to determine a s number of hemodynamic vascular parameters of an individual. These parameters which are of clinical importance include, but are not limited to:

v—The viscosity of the blood. Some blood problems or flow problems can be detected by monitoring the changes in this parameter.

$\rho$—The density of the blood. Dehydration and other blood related conditions can be detected by monitoring changes in this parameter.

R—The relaxed blood vessel radius. This radius is not the actual vessel radius but the effective radius of all the vessels in the area. Some data on the peripheral resistance can be acquired from this measurement.

EH—This value is indicative of the stiffness or lack of elasticity of the artery in the measured area. Problems related to high blood pressure oftentimes appear as a result of this condition.

$C_0$—Phase velocity of the forward propagated wave. This value is indicative of the blood pressure and it's fluctuations.

Figure 11:
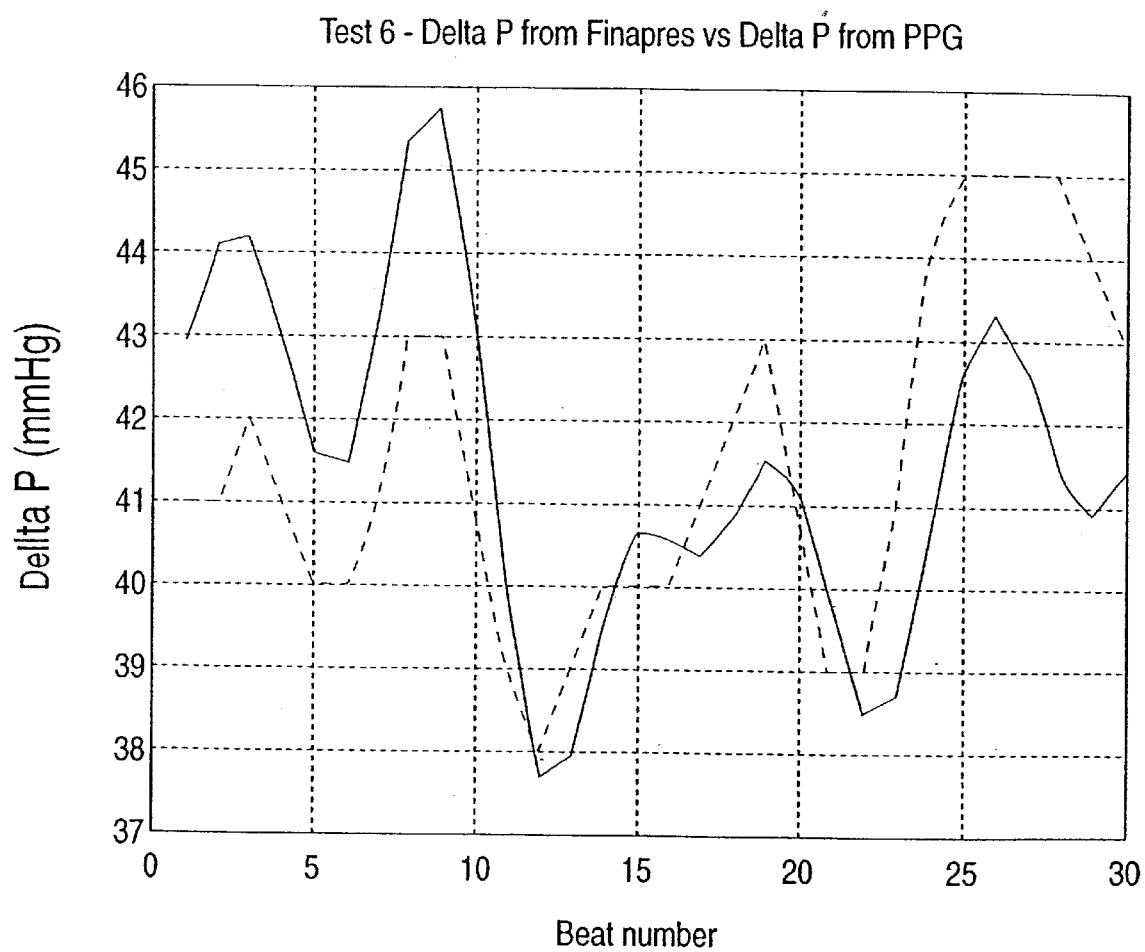
FIG. 11 is a graph displaying the quality of the measurement obtained by the system of the present invention as compared to a blood pressure signal obtained by the FINAPRES system (dotted line)
Figure 12:
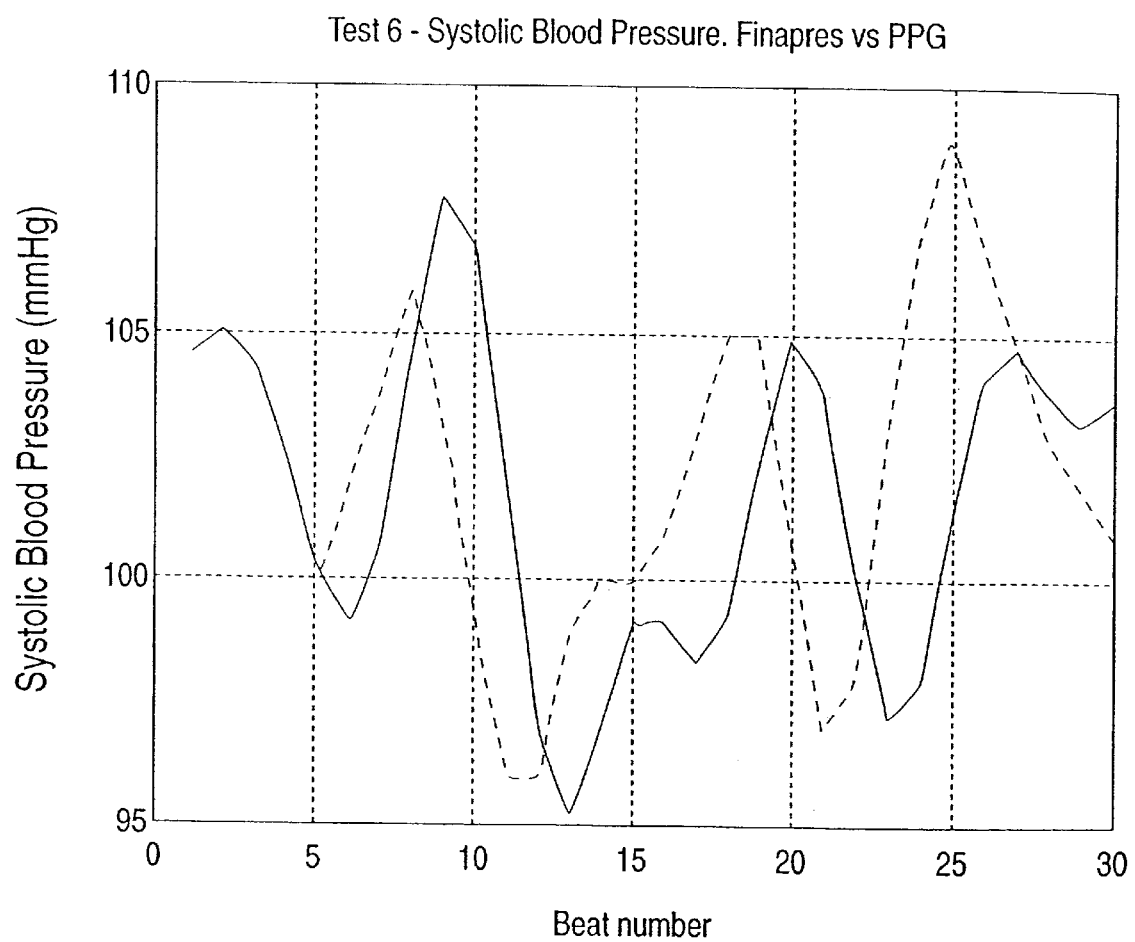
FIG. 12 is a graph displaying the systolic pressure obtained by the system of the present invention compared to the systolic pressure obtained by the FINAPRES system.
Figure 13:
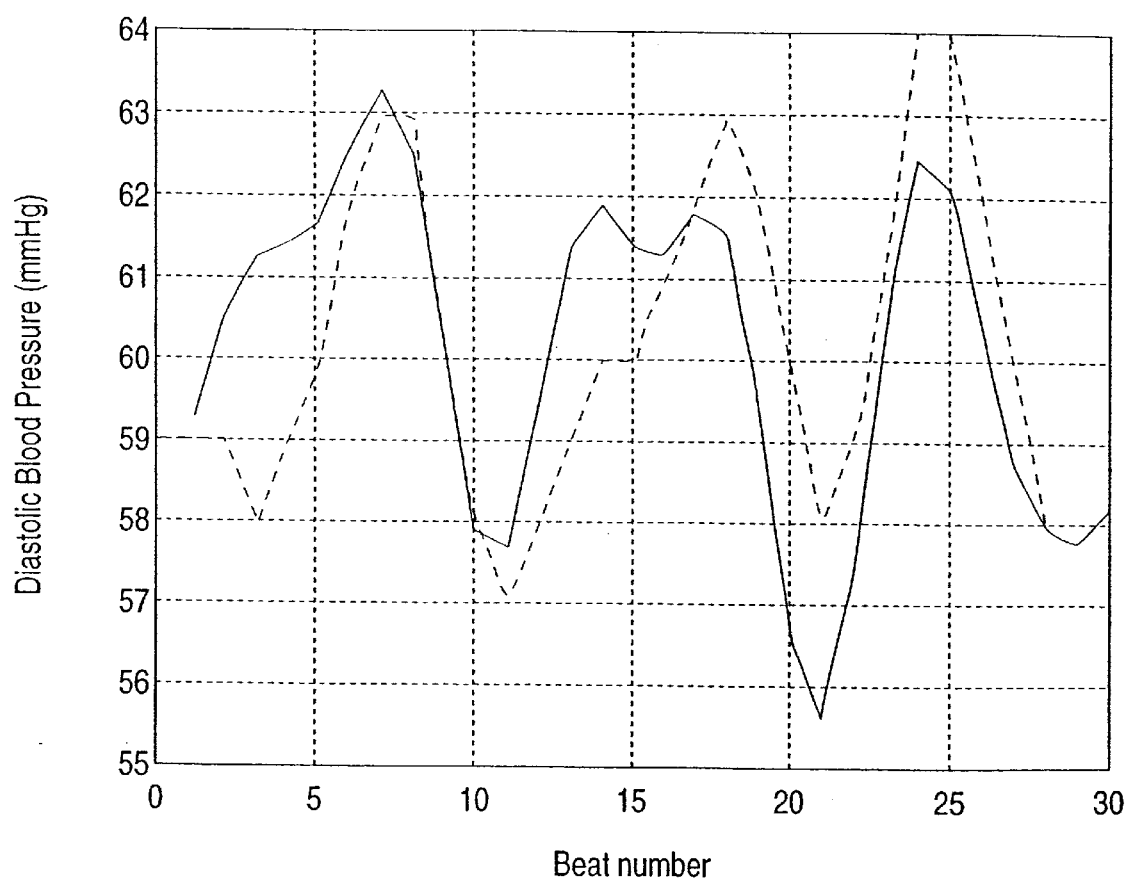
FIG. 13 is a graph displaying the diastolic pressure obtained by the system of the present invention compared to the diastolic pressure obtained by the FINAPRES system.

While reducing the present invention to practice several hemodynamic vascular parameters were obtained by processing, via the above described Equations, data collected by the photoplethysmograph detectors. The resultant hemodynamic vascular parameter information was compared to hemodynamic vascular parameter measurements taken by the FINAPRES system. FIG. 11 represents a computed pulse pressure, while FIGS. 12–13 represent computed systolic and diastolic pressures (respectively) all obtained as described hereinabove by the system of the present invention and compared to similar parameters measured by the FINAPRES system.

Calculating the Continues BP Waveform:

Projection of the measured signal from the PPG detectors with respect to the systolic and diastolic values calculated hereinabove enables to obtain a continues BP signal which can be described as follows:

$$P(t) = P_s - \rho C_0^2 \ln\left(\frac{\frac{v_s}{g} - \varepsilon_{bais}}{\frac{v(t)}{g} - \varepsilon_{bais}}\right) \tag{44}$$

Figure 14:
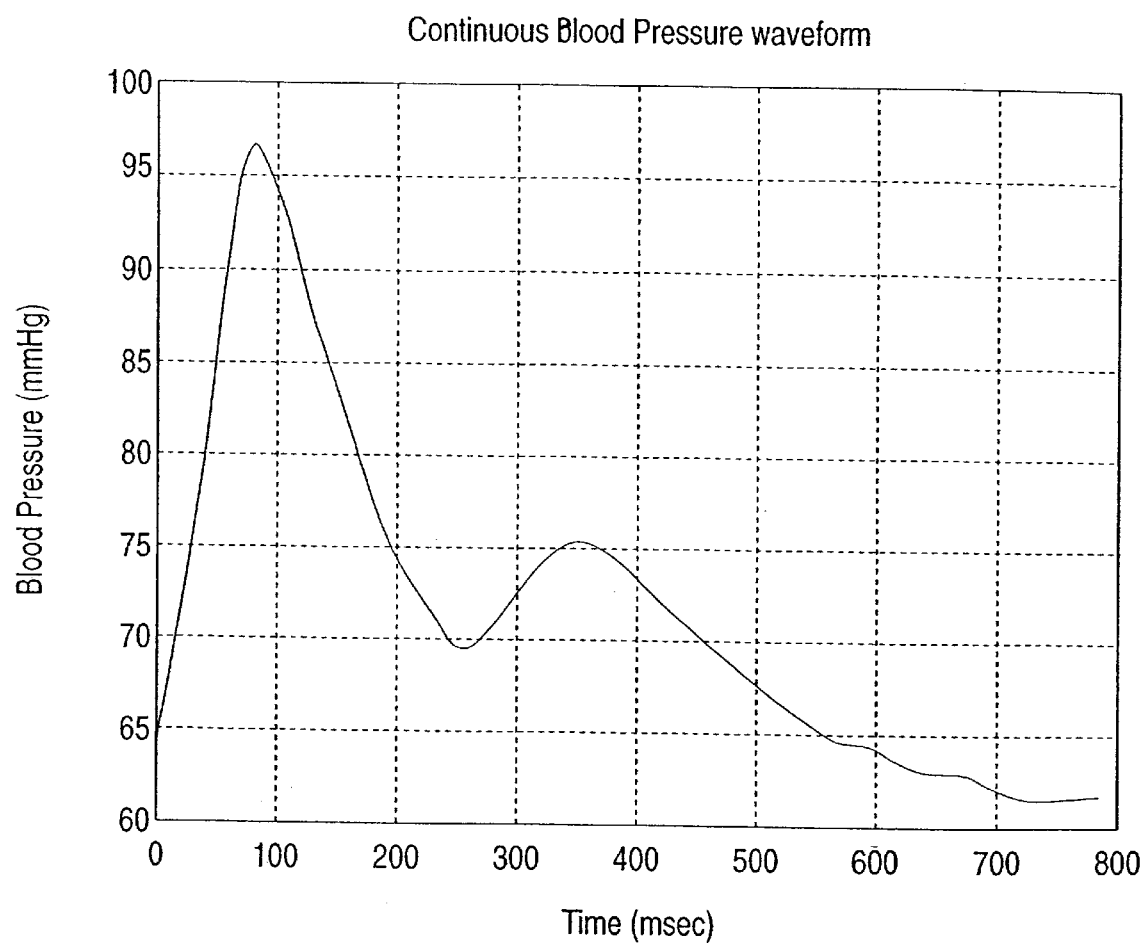
FIG. 14 is a graph displaying a single beat continuous waveform as obtained by the system of the present invention.

This Equation is derived from Equation 41 and details the blood pressure as a function of the measured signal v(t) and other parameters which were described hereinabove. FIG. 14 represents a one heart beat continuous blood pressure waveform translated into a continuous blood pressure measurement.

Example 4

Extracting Values Pertaining to Displacement of a Vessel Wall Under the Assumption that the Reflection Coefficient is Constant with Respect to the Frequency of the Harmonic Number To extract values pertaining to displacement of a vessel wall, the following assumptions are made: (i) the reflection coefficient is equal, $\gamma_n=\gamma_m$, for every pair of harmonics; (ii) the distance to the reflection site is equal for every pair of harmonics: (iii) there is no significant attenuation of the pressure wave between the detectors; (iv) there is no energy transfers between the different harmonics; and (v) the phase difference between the signals of the two PPG detectors is small.

For every pair of harmonics the vessel wall displacement is given by the following equations:

$$\eta_{1n}=A_n(1+\gamma_n \cdot e^{i-\psi_n(2l+2L)}) \quad \eta_{2n}=A_n(e^{i-\psi_n l}+\gamma_n \cdot e^{i-\psi_n(l+2L)}) \quad (45)$$

$$\eta_{1m}=A_m(1+\gamma_m \cdot e^{i-\psi_m(2l+2L)}) \quad \eta_{2m}=A_m(e^{i-\psi_m l}+\gamma_m \cdot e^{i-\psi_m(l+2L)}) \quad (46)$$

$A_n$, $A_m$ can be eliminated by reducing the number of equations to two, as follows:

$$\eta_{1n}(e^{i-\psi_n l}+\gamma_n \cdot e^{i-\psi_n(l+2L)})=\eta_{2n}(1+\gamma_n \cdot e^{i-\psi_n(2l+2L)}) \quad \eta_{1m}(e^{i-\psi_m l}+\gamma_m \cdot e^{i-\psi_m(l+2L)})=\eta_{2m}(1+\gamma_m \cdot e^{i-\psi_m(2l+2L)}) \quad (47)$$

By rearrangement one obtains the following equation:

$$\gamma_n e^{i \cdot \psi_m(2L)} = \frac{\eta_{2n} - \eta_{1n} e^{i \cdot \psi_n l}}{\eta_{1n} e^{i \cdot \psi_n l} - \eta_{2n} e^{2 \cdot i \cdot \psi_n l}} \quad (48)$$

$$\gamma_m e^{i \cdot \psi_m(2L)} = \frac{\eta_{2m} - \eta_{1m} e^{i \cdot \psi_m l}}{\eta_{1m} e^{i \cdot \psi_n l} - \eta_{2m} e^{2 \cdot i \cdot \psi_m l}}$$

Every equation from (48) can be presented as two equations, one for the reflection coefficient and another for the distance to the reflection site, as follows:

$$\gamma_n = \left|\frac{\eta_{2n} - \eta_{1n} e^{i \cdot \psi_n l}}{\eta_{1n} e^{i \cdot \psi_n l} - \eta_{2n} e^{2 \cdot i \cdot \psi_n l}}\right| \quad (49)$$

$$\gamma_m = \left|\frac{\eta_{2m} - \eta_{1m} e^{i \cdot \psi_m l}}{\eta_{1m} e^{i \cdot \psi_n l} - \eta_{2m} e^{2 \cdot i \cdot \psi_m l}}\right|$$

$$L_n = \text{Arg}\left(\frac{\eta_{2n} - \eta_{1n} e^{i \cdot \psi_n l}}{\eta_{1n} e^{i \cdot \psi_n l} - \eta_{2n} e^{2 \cdot i \cdot \psi_n l}}\right) \cdot \frac{1}{2\psi_n} \quad (50)$$

$$L_m = \text{Arg}\left(\frac{\eta_{2m} - \eta_{1m} e^{i \cdot \psi_m l}}{\eta_{1m} e^{i \cdot \psi_n l} - \eta_{2m} e^{2 \cdot i \cdot \psi_m l}}\right) \cdot \frac{1}{2\psi_m}$$

By using the following first order approximations:

$$e^{2i\psi_n l}=1+2i\psi_n l \quad (51)$$

$$e^{i\psi_n l}=1+i\psi_n l \quad (52)$$

the following equations can be obtained for every m & n:

$$\gamma_n = \left|\frac{\eta_{2n} - \eta_{1n} \cdot (1+i \cdot \psi_n l)}{\eta_{1n} \cdot (1+i \cdot \psi_n l) - \eta_{2n} \cdot (1+2 \cdot i \cdot \psi_n l)}\right| \quad (53)$$

$$L_n = \text{Arg}\left(\frac{\eta_{2n} - \eta_{1n} \cdot (1+i \cdot \psi_n l)}{\eta_{1n} \cdot (1+i \cdot \psi_n l) - \eta_{2n} \cdot (1+2 \cdot i \cdot \psi_n l)}\right) \cdot \frac{1}{2\psi_n} \quad (54)$$

$$\gamma_m = \left|\frac{\eta_{2m} - \eta_{1m} \cdot (1+i \cdot \psi_m l)}{\eta_{1m} \cdot (1+i \cdot \psi_m l) - \eta_{2m} \cdot (1+2 \cdot i \cdot \psi_m l)}\right| \quad (55)$$

$$L_m = \text{Arg}\left(\frac{\eta_{2m} - \eta_{1m} \cdot (1+i \cdot \psi_m l)}{\eta_{1m} \cdot (1+i \cdot \psi_m l) - \eta_{2m} \cdot (1+2 \cdot i \cdot \psi_m l)}\right) \cdot \frac{1}{2\psi_m} \quad (56)$$

In order to solve the above equation system, the constrain that $L_n=L_m$ and $\gamma_n=\gamma_m$ must be imposed.

Example 5

Using Three Equally Spaced Apart PPG Detectors in Order to Cancel Out the Reflected Wave While Calculating the Forward Propagating Wave Velocity In order to calculate the forward propagating wave velocity using three equally spaced apart PPG detectors, the following assumptions must be made: (i) the reflection coefficient is equal, $\gamma_n=\gamma_m$, for every pair of harmonics; (ii) the distance to the reflection site is equal for every pair of harmonics; (iii) there is no significant attenuation of the pressure wave between the detectors; (iv) there is no energy transfer between the different harmonics; (v) the phase difference between the signals of the two PPG detectors is small; and (vi) the three detectors have to be equally spaced apart.

When using three equally spaced detectors one obtains the following set of equations for the wall displacement:

$$\eta_{1n}=A_n(1+\gamma_n \cdot e^{i-\psi_n(4l+2L)}) \quad \eta_{2n}=A_n(e^{i-\psi_n l}+\gamma_n \cdot e^{i-\psi_n(3l+2L)}) \quad \eta_{3n}=A_n(e^{2-\psi_n l}+\gamma_n \cdot e^{i-\psi_n(2l+2L)}) \quad (56)$$

The term $\gamma_n e^{2i\psi_n L}$ can be eliminated to obtain the following pair of equations:

$$\eta_{1n}-\eta_{2n} \cdot e^{i-\psi_n l}=A_n(1-e^{2-i-\psi_n l})\eta_{3n}-\eta_{2n} \cdot e^{-i-\psi_n l}=A_n(e^{2-i-\psi_n l}-1) \quad (57)$$

$A_n$ can be eliminated to obtain the following equation:

$$(\eta_{3n}-\eta_{2n}e^{-i-\psi_n l})\cdot(1-e^{2-i-\psi_n l})=(\eta_{1n}-\eta_{2n}e^{i-\psi_n l})\cdot(e^{2-i-\psi_n l}-1) \quad (58)$$

Mathematical simplification of equation 58 generates the following:

$$\eta_{1n}-\eta_{2n}e^{-i-\psi_n l}-\eta_{3n}+\eta_{2n}e^{i-\psi_n l}=0 \quad (59)$$

By using the following identity:

$$\cos(x) = \frac{e^{ix} + e^{-ix}}{2}, \quad (60)$$

one can obtain:

$$\psi_n = \cos^{-1}\left(\frac{\eta_{3n} - \eta_{1n}}{2 \cdot \eta_{2n}}\right)/l \quad (61)$$

The following values are obtained for the other variables when equation (61) is substituted into equations (57) and (58):

$$A_n = \frac{\eta_{1n} - \eta_{2n} e^{i \cdot \psi_n l}}{1 - e^{2 \cdot i \cdot \psi_n l}} \quad (62)$$

$$\gamma_n = \left|\frac{\eta_{1n} - \eta_{2n} \cdot e^{-i \cdot \psi_n l}}{e^{4 \cdot i \cdot \psi_n l} - e^{2 \cdot i \cdot \psi_n l}} \cdot \frac{1 - e^{2 \cdot i \cdot \psi_n l}}{\eta_{1n} - \eta_{2n} \cdot e^{i \cdot \psi_n l}}\right| = \left|\frac{\eta_{1n} - \eta_{2n} \cdot e^{-i \cdot \psi_n l}}{\eta_{2n} \cdot e^{i \cdot \psi_n l} - \eta_{1n}}\right| \quad (63)$$

$$L_n = \frac{1}{2} \cdot \text{Ln}\left(\frac{\eta_{1n} - \eta_{2n} \cdot e^{-i \cdot \psi_n l}}{\eta_{2n} \cdot e^{i \cdot \psi_n l} - \eta_{1n}} \cdot \frac{1}{\gamma_n}\right) \quad (64)$$

Example 6

Measuring the Foot to Foot Speed and Solving the Equation of the Wall Displacement in Order to Calculate the Forward Propagating Wave In this method, the foot to foot speed is obtained and used as an approximation to the forward wave velocity of the fifth harmonic. From the fifth harmonic the distance to the reflection point is obtained and then used to solve the other harmonics.

This is performed under the following assumptions: (i) the reflection coefficient is equal, $\gamma_n=\gamma_m$, for every pair of harmonics; (ii) the distance to the reflection site is equal for every pair of harmonics; (iii) there is no significant attenuation of the pressure wave between the detectors; (iv) there is no energy transfers between the different harmonics; (v) the phase difference between the signals of the two PPG detectors is small; (vi) the foot to foot velocity is a good approximation for the velocity of the forth harmonic (Vascular Dynamics—N. Westerhof, D. R. Gross—PLENUM—1989)

The propagation velocity is calculated by measuring the time difference between the two detectors (see Vascular Dynamics—N. Westerhof, D. R. Gross—PLENUM—1989). In this measurement only the mean velocity is obtained but by assuming that the mean velocity equals to the forth harmonic propagation velocity enables to solve the following equations in order to obtain the reflection coefficient and the distance to the reflection site.

The phase velocity is given by the following equation:

$$\psi_n = \frac{2\pi n}{60} \cdot \frac{\Delta t}{l} \cdot HR \tag{65}$$

The following equations describe the wall displacement:

$$\eta_{1n} = A_n(1+\gamma_n \cdot e^{i-\eta(2l+2L)})\eta_{2n} = A_n(e^{i-\psi_n l}+\gamma_n \cdot e^{i-\psi_n(l+2L)}) \tag{66}$$

By using the methods described under Examples 4 and 5 above, one can obtain the following equations:

$$\gamma_n = \left|\frac{\eta_{1n} \cdot e^{i \cdot \psi_n l} - \eta_{2n}}{\eta_{2n} \cdot e^{i \cdot \psi_n l} - \eta_{1n}}\right| \tag{67}$$

$$L_n = \text{Arg}\left(\frac{\eta_{1n} \cdot e^{i \cdot \psi_n l} - \eta_{2n}}{\eta_{2n} \cdot e^{i \cdot \psi_n l} - \eta_{1n}}\right) \cdot \frac{l}{2\psi_n} - l \tag{68}$$

For the forth harmonic one can calculate the values of $L_n$ and $\gamma_n$ and then the value for the propagation velocity by using the following equation for each harmonic:

$$\psi_n = \frac{-iP_{1n}(l+\gamma(2L+l)) \pm i\sqrt{(P_{1n}(l+\gamma(2L+l)))^2 + 4(l+\gamma)(P_{1n}-P_{2n})P_{2n}(2L+l)l\gamma}}{2P_{2n}(2L+l)l\gamma} \tag{69}$$

Example 7

Calculating Both the Flow and the Wall Displacement from the Signal Obtained by the PPG Detectors and then Extracting Values for the Wall Displacement (pressure) and Blood Flow This method processes the PPG signal with respect to time and flow. The obtained impedance of the blood vessel is utilized to calculate the forward propagated wave and the backward propagated wave.

This is performed under the following assumptions: (i) the reflection coefficient is equal, $\gamma_n = \gamma_m$, for every pair of harmonics; (ii) the distance to the reflection site is equal for every pair of harmonics; (iii) There is no significant attenuation of the pressure wave between the detectors; (iv) no energy transfers between the different harmonics; (v) the phase difference between the signals of the two PPG detector is small; (vi) the radius and pressure of the blood vessel are in linear association; (vii) the relationship between the pressure ($P_n$) and the flow ($F_n$) is $P_n = F_n \cdot Z_n$, when $Z_n = \psi_n/\omega_n$; and (viii) the blood flow in the vessel has a linear relation to the cross section of the vessel $$F_n = \left(\alpha\pi\left(\frac{\partial \eta_n}{\partial t}\right)\right)^2.$$

The following definitions are used throughout this Example:

| | |
|---|---|
| $F_{1n}$ | The $n^{th}$ harmonic of the blood flow as measured in the first detector. |
| $F_{2n}$ | The $n^{th}$ harmonic of the blood flow as measured in the second detector. |
| $P_{1n}$ | The $n^{th}$ harmonic of the blood pressure as measured in the first detector. |
| $P_{2n}$ | The $n^{th}$ harmonic of the blood pressure as measured in the second detector. |
| $\gamma_n$ | Reflection coefficient. |
| $\eta_{1n}$ | The $n^{th}$ harmonic of the wall displacement as measured in the first detector. |
| $\eta_{2n}$ | The $n^{th}$ harmonic of the wall displacement as measured in the second detector. |
| $A_n$ | The $n^{th}$ harmonic of the forward propagate pressure wave. |
| $\psi_n$ | Phase difference for the $n^{th}$ harmonic. |
| | Radial velocity of the harmonic |
| | Distance between the detectors |
| L | Distance to the reflection site. |
| a,fl | calibration coefficients of the system. |
| $\omega_n$ | Radial velocity of the harmonic |
| l | Distance between the detectors |
| L | Distance to the reflection site. |
| $\alpha, \beta$ | calibration coefficients of the system. |

The following equations represent the pressure inside the vessel:

$$P_{1n} = A_n(1+\gamma_n \cdot e^{i-\psi_n(2L+2l)})P_{2n} = A_n(e^{i-\psi_n l}+\gamma_n \cdot e^{i-\psi_n(l+2L)}) \tag{70}$$

Working under the above assumptions the following equations for the blood flow inside the blood vessel are obtained:

$$F_{1n} = \frac{\omega_n}{\psi_n} A_n(1 - \gamma_n \cdot e^{i\psi_n(2L+2l)}) \tag{71}$$

$$F_{2n} = \frac{\omega_n}{\psi_n} A_n(e^{i\psi_n l} - \gamma_n \cdot e^{i\psi_n(2L+l)})$$

The following relations are also obtained under the above assumptions:

$$F_{2n} = \pi\beta\left(\frac{\partial \eta_{2n}}{\partial t}\right)^2, F_{1n} = \pi\beta\left(\frac{\partial \eta_{1n}}{\partial t}\right)^2, P_{2n} = \alpha\eta_{2n}, P_{1n} = \alpha\eta_{1n} \tag{72}$$

By substituting the above relations into Equations (70) and (71) one obtains the following equation system:

$$\alpha\eta_{1n} = A_n(1+\gamma_n \cdot e^{i-\psi_n(2L+2l)})\alpha\eta_{2n} = A_n(e^{i-\psi_n l}+\gamma_n \cdot e^{i-\psi_n(l+2L)}) \tag{73}$$

$$\pi\beta\left(\frac{\partial \eta_{1n}}{\partial}\right)^2 = \frac{\omega_n}{\psi_n}A_n(1-\gamma_n \cdot e^{i\psi_n(2l+2L)}) \tag{74}$$

$$\pi\beta\left(\frac{\partial \eta_{2n}}{\partial}\right)^2 = \frac{\omega_n}{\psi_n}A_n(e^{i\psi_n l} - \gamma_n \cdot e^{i\psi_n(l+2L)})$$

By measuring the value of l and approximating the value for L one can obtain the following equation system:

$$(e^{i\psi_n l} - \gamma_n e^{i\psi_n(l+2L)})\left(\frac{\partial \eta_{1n}}{\partial t}\right)^2 = (1 - \gamma_n e^{i\psi_n(2l+2L)})\left(\frac{\partial \eta_{2n}}{\partial t}\right)^2 \quad (75)$$

$$\eta_{1n}(e^{i\psi_n l} - \gamma_n \cdot e^{i\psi_n(l+2L)}) = \eta_{2n}(1 + \gamma_n e^{i\psi_n(2l+2L)}) \quad (76)$$

Due to the small size of the measured phase difference the following first order approximations can be utilized:

$$e^{i-\psi_n l} = 1 + i\psi_n l$$
$$e^{i-\psi_n(l+2L)} = 1 + i\psi_n(l+2L)$$
$$e^{i-\psi_n(2L+2l)} = 1 + i\psi_n(2L+2l)$$

By inserting these approximations into Equations (75) and (76) one obtains the following equations:

$$((1 - \gamma_n)(1 + i\psi_n l) - 2iL\gamma_n\psi_n)\left(\frac{\partial \eta_{1n}}{\partial t}\right)^2 = \quad (77)$$
$$(1 - \gamma_n)(1 + i\psi_n(2l+2L))\left(\frac{\partial \eta_{2n}}{\partial t}\right)^2$$

$$\eta_{1n}(1+i\psi_n l - \gamma_n \cdot (1+i\psi_n(l+2L))) = \eta_{2n}(1+\gamma_n \cdot (1+i\psi_n(2l+2L))) \quad (78)$$

After solving this pair of equations, the values for $\gamma_n$ and $\psi_n$ are obtained:

$$\gamma_n = \frac{\eta_{2\eta} - \eta_{1\eta}(1 + i\psi_n l)}{2 + i\psi_n(3l + 4L)} \quad (79)$$

$$-\psi_n^2\left(\eta_{1\eta}(l+4L) + (3l+4L)\left(\frac{\partial \eta_{1n}}{\partial t}\right)^2\right) + \quad (80)$$
$$i\psi_n(3l+4L)\left(\left(\frac{\partial \eta_{1n}}{\partial t}\right)^2 - \left(\frac{\partial \eta_{2n}}{\partial t}\right)^2\right) +$$
$$\ldots (\eta_{1\eta} - \eta_{2\eta})(l+4L) + 2\left(\left(\frac{\partial \eta_{1n}}{\partial t}\right)^2 - \left(\frac{\partial \eta_{2n}}{\partial t}\right)^2\right) = 0$$

Thus, the system and method of the present invention enable continuous monitoring of hemodynamic vascular parameters such as, for example, blood pressure, by using a non-invasive technique which provides a high degree of accuracy and yet can easily be practiced by non-skilled personnel.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety. Citation or identification of any reference in this application shall not be construed as an admission that such reference is available as prior art to the present invention.

What is claimed is:

1. A system for non-invasively monitoring at least one hemodynamic vascular parameter of an individual, the system comprising:
   (a) at least two infrared detectors being positionable in a spaced apart configuration against a region of a skin of the individual above at least one blood vessel, each of said at least two infrared detectors being for individually collecting infrared spectral data from said region of the skin, said infrared spectral data corresponding to a volume of blood present within said at least one blood vessel; and
   (b) a processing unit being in communication with said at least two infrared detectors, said processing unit being for independently processing said infrared spectral data collected by each of said at least two infrared detectors, said processing unit implementing an algorithm serving to account for blood reflection waves resulting from reflection sites in blood vessels, so as to yield information pertaining to the at least one hemodynamic vascular parameter of the individual.

2. The system of claim 1, wherein each of said at least two infrared detectors detects changes in infrared reflection from said region of said skin.

3. The system of claim 1, wherein each of said at least two infrared detectors includes an infrared source for irradiating said region of said skin and an infrared sensor for sensing infrared reflection reflected from said region of the skin.

4. The system of claim 3, wherein said infrared source irradiates said region with infrared radiation of a wavelength within a range of 800 nm to 960 nm.

5. The system of claim 1, wherein each of said at least two infrared detectors is an infrared photoplethysmograph.

6. The system of claim 1, wherein said at least two infrared detectors include three detectors each independently being for collecting infra red spectral emission data from said region, said three detectors being positionable in a spaced apart configuration against said region of said skin.

7. The system of claim 1, wherein the at least one hemodynamic vascular parameter is selected from the group consisting of blood viscosity, blood density, a radius of said blood vessel, an elasticity of said blood vessel, systolic blood pressure, diastolic blood pressure and continuous blood pressure.

8. The system of claim 1, wherein said infra red spectral data is collected by each of said at least two infrared detectors over the course of at least one heart beat cycle.

9. The system of claim 1, wherein said infra red spectral data is continuously collected by each of said at least two infrared detectors, thus enabling continuous monitoring of the at least one hemodynamic vascular parameter.

10. The system of claim 1, further comprising a device being for obstructing flow in said blood vessel down stream from said region of said skin.

11. The system of claim 1, further comprising an interface communicating with said processing unit, said interface being for providing information pertaining to the at least one hemodynamic vascular parameter to an operator of the system.

12. The system of claim 11, wherein said information pertaining to the at least one hemodynamic vascular parameter is provided to said operator in at least one format selected from the group consisting of a textual format, a graphic format and an audio format.

13. The system of claim 1, wherein said algorithm calculates said information pertaining to the at least one hemodynamic vascular parameter of the individual by determining a wave propagation velocity, a reflection coefficient and a distance to a reflection site.

14. The system of claim 1, wherein said algorithm calculates said information pertaining to the at least one hemodynamic vascular parameter of the individual by extracting values pertaining to displacement of a vessel wall under an assumption that a reflection coefficient is constant with respect to a frequency of a specific harmonic.

15. The system of claim 1, wherein said algorithm calculates said information pertaining to the at least one hemodynamic vascular parameter of the individual taking into account information pertaining to a foot to foot speed and calculating a wall displacement in order to calculate a forward propagating wave.

16. The system of claim 1, wherein said algorithm calculates said information pertaining to the at least one hemodynamic vascular parameter of the individual by extracting values pertaining to wall displacement and blood flow.

17. A method of non-invasively monitoring at least one hemodynamic vascular parameter of an individual, the method comprising:

(a) positioning at least two infrared detectors in a spaced apart configuration against a region of a skin of the individual above at least one blood vessel;

(b) individually collecting in each of said infrared detectors, infrared spectral data from said region of the skin, said infrared spectral data corresponding to a volume of blood present within said at least one blood vessel; and (b) independently processing said infrared spectral data collected by each of said at least two infrared detectors, while accounting for blood reflection waves resulting from reflection sites in blood vessels, so as to yield information pertaining to the at least one hemodynamic vascular parameter of the individual.

18. The method of claim 17, wherein each of said at least two infrared detectors includes an infrared source for irradiating said region of said skin and an infrared sensor for sensing infrared reflection reflected from said region of the skin.

19. The method of claim 18, wherein said infrared source irradiates said region with infrared radiation of a wavelength within a range of 800 nm to 960 nm.

20. The method of claim 17, wherein each of said at least two infrared detectors is an infrared photoplethysmograph.

21. The method of claim 17, wherein said at least two infrared detectors include three detectors each independently being for collecting infra red spectral emission data from said region, said three detectors being positionable in a spaced apart configuration against said region of said skin.

22. The method of claim 17, wherein said at least one blood vessel includes an artery underlying said region of said skin.

23. The method of claim 17, wherein the at least one hemodynamic vascular parameter is selected from the group consisting of blood viscosity, blood density, a radius of said blood vessel, an elasticity of said blood vessel, systolic blood pressure, diastolic blood pressure and continuous blood pressure.

24. The method of claim 17, wherein said step of individually collecting in each of said infrared detectors, infrared spectral data from said region of the skin, is effected over the course of at least one heart beat cycle.

25. The method of claim 17, wherein said step of individually collecting in each of said infrared detectors, infrared spectral data from said region of the skin, is effected continuously thus enabling continuous monitoring of the at least one hemodynamic vascular parameter.

26. The method of claim 17, further comprising the step of obstructing flow in said blood vessel down stream from said region of said skin prior to said step of collecting in each of said infrared detectors, infrared spectral data from said region of the skin.

27. The method of claim 17, wherein accounting for blood reflection waves resulting from reflection sites in blood vessels is by determining a wave propagation velocity, a reflection coefficient and a distance to a reflection site.

28. The method of claim 17, wherein accounting for blood reflection waves resulting from reflection sites in blood vessels is by extracting values pertaining to motion of a vessel wall under an assumption that a reflection coefficient is constant with respect to a frequency of a specific harmonic.

29. The method of claim 17, wherein accounting for blood reflection waves resulting from reflection sites in blood vessels is by calculations taking into account information pertaining to a foot to foot speed and calculating a wall displacement in order to calculate a forward propagating wave.

30. The method of claim 17, wherein accounting for blood reflection waves resulting from reflection sites in blood vessels is by extracting values pertaining to wall displacement and blood flow.

* * * * *